United States Patent [19]

Sohda et al.

[11] Patent Number: 5,747,486
[45] Date of Patent: May 5, 1998

[54] THIENOPYRIDINE OR THIENOPYRIMIDINE DERIVATIVES AND THEIR USE

[75] Inventors: Takashi Sohda, Osaka; Haruhiko Makino; Atsuo Baba, both of Hyogo, all of Japan

[73] Assignee: Takeda Chemical Industries, Osaka, Japan

[21] Appl. No.: 571,915

[22] PCT Filed: Nov. 7, 1995

[86] PCT No.: PCT/JP95/02271

§ 371 Date: Dec. 27, 1995

§ 102(e) Date: Dec. 27, 1995

[87] PCT Pub. No.: WO96/14319

PCT Pub. Date: May 17, 1996

[30] Foreign Application Priority Data

Nov. 8, 1994 [JP] Japan ................. 6-273801
Dec. 22, 1994 [JP] Japan ................. 6-320055

[51] Int. Cl.$^6$ ............ A61K 31/54; A61K 31/535; C07D 401/02; C07D 403/02
[52] U.S. Cl. ............ 514/211; 514/212; 514/213; 514/215; 514/217; 514/228.2; 514/228.8; 514/232.8; 514/233.8; 514/234.5; 514/235.2; 514/235.5; 514/235.8; 514/301; 514/258; 514/267; 514/291; 514/292; 546/80; 546/83; 546/114; 546/89; 544/253; 544/117; 544/127
[58] Field of Search ............ 546/114, 198, 546/199, 80, 83, 89; 544/253, 117, 127; 514/212, 213, 215, 217, 228.2, 228.8, 232.8, 233.8, 234.5, 235.2, 235.5, 235.8, 258, 267, 291, 292, 301

[56] References Cited

FOREIGN PATENT DOCUMENTS

| 0 194 416 | 9/1986 | European Pat. Off. . |
| 51-43796 | 4/1976 | Japan . |
| 52-46095 | 4/1977 | Japan . |
| 61-176591 | 8/1986 | Japan . |

OTHER PUBLICATIONS

Attaby et al., "Reactions with Cyanothioacetamide Derivatives: Synthesis and Reactions of Some Pyrazolo[3,4-b] Pyridine Derivatives" *Phosphorous, Sulfur and Silicon*, vol. 73:127-135, (1992).

Elgemeie et al., "α,β-Unsaturated Nitriles in Heterocyclic Synthesis. Novel Synthesis of Pyridines and Thienol[2,3-b] pyridine Derivative", *Bull. Chem. Soc. Jpn.*, vol. 61:4431-4433, (1988).

Adachi et al., "Studies on Dihydrophyridines. III. Synthesis of 4,7-Dihydrothienol[2,3-b]-pyridines With Vasodilator and Antihypertensive Activities", *Chem. Pharm. Bull.*, vol. 36(11):4389-4402, (1988).

Toulhoat et al., "Complexes Macrocycliques Organophosphores du Palladium II. P-Alkyles et a Ponts Satures et Insatures", *Phosphorus, Sulfur, and Silicon*, vol. 71:127-138, (1992).

Ueno et al., "Electrochemical Oxidation of Methyl (±)-4,7-Dihydro-3-isobutyl-6-methyl-4-(3-mitrophenyl)-thieno-[2,3-b]pyridine-5-carboxylate, a New Type of Dihydropyridine Calcium Blocker," *Chem. Pharm. Bull.*, vol. 40(6):1376-1382 (1992).

A. A. Kpayse et al., *Khim. Geterotsikl. Soedin.*, vol. 1:124-128 (1987).

Joan Foretea, "Thieno[2,3-d]pyrimidine 3-oxides. Synthesis and N-Oxide Reactions of 4-Phenyl-and 4-Aminothieno[2,3-d][1,4] pyrimidine 3-Oxides", *Journal fur praktische Chemie*, vol. 317:705-711, (1975).

Nakanishi et al., "Studies on Psychotropic Drugs. Synthesis and Structure-Activity Relationships of 5-Phenyl-1, 3-dihydro-2H-thienol[2,3-e] diazepin-e-ones", *Journal of Medicinal Chemistry*, vol. 16(3):214-219 (1973).

Tinney et al., "Synthesis and Pharmacological Evaluation of 2,3-Dihydro-1H-thieno[2,3-e][1,4] diazepines", *Journal of Medicinal Chemistry*, vol. 17(6):624-630, (1974).

*Primary Examiner*—Matthew V. Grumbling
*Attorney, Agent, or Firm*—Foley & Lardner

[57] ABSTRACT

This invention provides an anti-inflammatory agent, particularly an agent for treating arthritis, and a bone resorption inhibiting agent, containing a thienopyridine or thienopyrimidine derivative or a salt thereof. This invention also provides a novel thienopyridine or thienopyrimidine derivative having anti-inflammatory activity and bone resorption inhibiting activity.

27 Claims, No Drawings

THIENOPYRIDINE OR THIENOPYRIMIDINE DERIVATIVES AND THEIR USE

This is a national phase application, filed under U.S.C. § 371 of PCT/JP95/02271, filed Nov. 7, 1995.

TECHNICAL FIELD

This invention relates to a novel thienopyridine or a novel thienopyrimidine derivative or a salt thereof, which is useful as an anti-inflammatory agent, especially a therapeutic agent of arthritis, and which is useful as a prophylactic or therapeutic agent against osteoporosis.

BACKGROUND ART

Arthritis is an inflammatory disease of the joint, and, as principal diseases, are mentioned rheumatoid arthritis and related diseases with joint inflammation.

Among them, especially rheumatoid arthritis, also called chronic arthrorheumatism, is a chronic multiple arthritis characterized by inflammatory changes in the synovial membrane of the articular internal capsule layer. Arthritic diseases like rheumatoid arthritis are progressive and cause joint disorders such as deformation and ankylosis, often resulting in severe physical disorder due to lack of effective treatment and subsequent deterioration.

Traditionally, these forms of arthritis have been chemotherapeutically treated with various agents, including steroids such as cortisone and other adrenocortical hormones; non-steroidal anti-inflammatory agents such as aspirin, piroxicam and indomethacin; gold agents such as aurothiomalate; anti-rheumatic agents such as chloroquine preparations and D-penicillamine; antipodagric agents such as colchicine; and immnunosuppressors such as cyclophosphamide, azathiopurine, methotrexate and levamisole.

However, these drugs have drawbacks such as severe adverse reactions, adverse reactions hampering the drug's long-term use, lack of sufficient efficacy and a failure to be effective against already-occurring arthritis.

Accordingly, development of a drug performing excellent prophylactic/therapeutic action on arthritis with low toxicity has still been desired from the clinical viewpoint.

Traditionally, various compounds have been synthesized as thieno[2,3-b]pyridine derivatives, which are disclosed in, for example, Bull. Chem. Soc. Jpn., 61, 4431 (1988), Chem. Pharm. Bull., 36, 4389 (1988), Phosphorus, Sulfur, and Silicon, 73, 127 (1992), Chem. Pharm. Bull., 40, 1376 (1992), and Khim. Geterotsikl. Soedin., 1, 124 (1987). In those compounds, the substituent at 6-position of the thieno [2,3-b]pyridine skeleton is restricted to methyl group. And, no description of anti-inflammatory activities is given on these known thienopyridine derivatives. In Journal fuer praktische Chemie, 317, 705 (1975), the synthesis of thieno [2,3-d]pyrimidine derivatives having methyl group or acetoxymethyl group at 2-position is described. And, in Japanese Patent Unexamined Publication (Kokai tokkyo koho) No. 43796/1976 [Chemical Abstracts, 85, 94398r (1976)], there are disclosed thieno[2,3-d]pyrimidine derivatives having carboxylethyl group at 2-position. However, there has been no report of any derivative having a carbon chain substituted with heterocyclic group or amino group at 2-position of these thieno[2,3-d]pyrimidine skeleton. And, no description of inhibitory activity of bone resorption is given on these known thienopyridine or thienopyrimidine derivatives.

DISCLOSURE OF INVENTION

The present inventors found that the novel thienopyridine or thienopyrimidine derivatives represented by the formula (I):

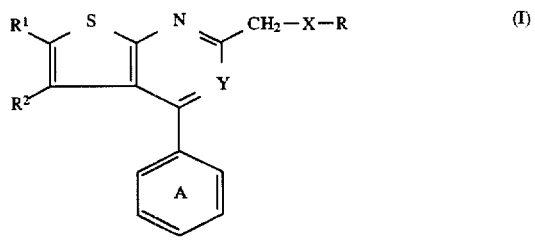

have anti-arthritic activity and are useful as a joint destruction suppressor and have inhibitory activity of bone resorption and are useful as a prophylactic or therapeutic agent against osteoporosis, and accomplished the present invention.

More specifically, the present invention relates to:
(1) A compound represented by the formula (I):

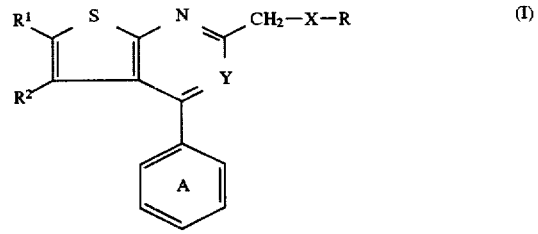

wherein $R^1$ and $R^2$ independently stand for a hydrogen atom, a halogen atom or an optionally substituted alkyl group, or $R^1$ and $R^2$ may be combined to form a 5- to 7-membered ring; Y stands for a nitrogen atom or C-G, G stands for an optionally esterified carboxyl group; X stands for an oxygen atom, an optionally oxidized sulfur atom or $-(CH_2)_q-$ (q denotes an integer of 0 to 5); R stands for an optionally substituted heterocyclic group or an optionally substituted amino group; and ring A may optionally be substituted, or a salt thereof.

(2) The compound of above item (1), wherein the optionally substituted alkyl group for $R^1$ or $R^2$ is independently a straight-chain or branched-chain $C_{1-6}$ alkyl group; the optionally substituted 5- to 7-membered ring for $R^1$ and $R^2$ is (i) a $C_{5-7}$ alicyclic hydrocarbon group, or (ii) a heterocyclic group containing one to 4 oxygen atom, one to 4 sulfur atom which may be oxidized, or one nitrogen atom which may be substituted by optionally substituted $C_{1-10}$ alkyl; the optionally substituted heterocyclic group for R is (i) a 5- to 7-membered heterocyclic group containing one sulfur atom, one nitrogen atom or one oxygen atom, (ii) a 5- to 6-membered heterocyclic group containing 2 to 4 nitrogen atoms, (iii) a 5- to 6-membered heterocyclic group containing 1 to 2 nitrogen atoms and one sulfur atom or one oxygen atom, or (iv) a group formed by condensation of each of the above three groups with a 6-membered group containing two or less nitrogen atom, a benzene ring or a 5-membered ring containing one sulfur atom; or the optionally substituted amino group for R is represented by $-N(R^3)$ $(R^4)$, in which $R^3$ and $R^4$ independently stand for a hydrogen atom, an optionally substituted hydrocarbon residue or an optionally substituted heterocyclic group, or $R^3$ and $R^4$ are combined to form a nitrogen containing cyclic group; and the substituent of ring A is substituted by a halogen atom, a nitro group, an optionally substituted alkyl group, an optionally substituted hydroxyl group, an optionally substituted thiol group, an optionally substituted amino group, an acyl group, an optionally esterified carboxyl group or an optionally substituted aromatic cyclic group.

(3) The compound of the above item (2), wherein an optionally substituted 5- to 7-membered ring for $R^1$ and $R^2$ is represented by the formula of $—R^1—R^2—$, which is $—(CH_2)_3—$, $—(CH_2)_4—$, $—(CH_2)_5$ . . $—CH_2—N(R^5)—CH_2—CH_2—$ ($R^5$ is $C_{1-4}$ alkyl which may be substituted by phenyl), $—CH_2—S—CH_2—CH_2—$, $—CH_2—SO—CH_2—CH_2—$, $—CH_2—SO_2—CH_2—CH_2—$, or $—CH_2—O—CH_2—CH_2—$.

(4) The compound of the above item (2), wherein the optionally substituted hydrocarbon residue for $R^3$ or $R^4$ is independently a $C_{1-8}$ saturated aliphatic hydrocarbon residue,
a $C_{2-8}$ unsaturated aliphatic hydrocarbon residue,
a $C_{3-7}$ saturated alicyclic hydrocarbon residue,
a $C_{5-7}$ unsaturated alicyclic hydrocarbon residue,
a $C_{4-9}$ alicyclic-aliphatic hydrocarbon residue,
a $C_{7-9}$ phenyl alkyl, a $C_{11-13}$ naphtyl alkyl, a phenyl or a naphthyl;

the optionally substituted heterocyclic group for $R^3$ or $R^4$ is independently (i) a 5- to 7-membered heterocyclic group containing one sulfur atom, one nitrogen atom or one oxygen atom, (ii) a 5- to 6-membered heterocyclic groups containing 2 to 4 nitrogen atoms, or (iii) a 5- to 6-membered heterocyclic group containing 1 to 2 nitrogn atoms and one sulfur atom or one oxygen atom, which may be condensed with a 6-membered ring containing one or two nitrogen atoms, benzene ring or a 5-membered ring containing one sulfur atom; and nitrogen containing cyclic group comprising $R^3$ and $R^4$ is 5- to 7-membered one.

(5) The optionally substituted heterocyclic group for $R^3$ or $R^4$ is independently an aromatic monocyclic-heterocyclic group, an aromatic condensed heterocyclic group, or a non-aromatic heterocyclic group.

(6) The compound of the above item (5), wherein (i) the aromatic monocyclic-heterocyclic group for $R^3$ or $R^4$ is independently furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl or triazinyl; (ii) the aromatic condensed heterocyclic group for $R^3$ or $R^4$ is independently benzofuranyl, isobenzofuranyl, benzo[b]thienyl, indolyl, isoindolyl, 1H-indazolyl, benzimidazolyl, benzoxazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,2-b]pyridazinyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl or 1,2,4-triazolo[4,3-b]pyridazinyl; or (iii) the non-aromatic heterocyclic groups for $R^3$ or $R^4$ is independently oxiranyl, azetidinyl, oxetanyl, thietanyl, pyrrolidinyl, tetrahydrofuryl, thiolanyl, piperidyl, tetrahydropyranyl, morpholinyl, thiomorpholinyl or piperazinyl.

(7) The compound of the above item (4), wherein the 5- to 7-membered nitrogen containing cyclic group for $R^3$ and $R^4$ is independently 1-pyrrolidinyl, 1-imidazolidinyl, 1-pyrazolidinyl, 1-piperidinyl, 1-piperazinyl, 4-morpholinyl, 4-thiomorpholinyl, homopiperazin-1-yl, pyrazol-1-yl, imidazol-1-yl, 1,2,4-triazol-1-yl, 1,3,4-triazol-1-yl, 1,2,3-triazol-1-yl, 1,2,3-triazol-2-yl, tetrazol-1-yl, benzimidazol-1-yl, indol-1-yl or indazol-1-yl.

(8) The compound of the above item (2), wherein the optionally substituted hydrocarbon residue for $R^3$ or $R^4$ is independently a straight- or a branched-chain $C_{1-6}$ alkyl.

(9) The compound of the above item (2), wherein as a substituent for ring A, (i) the halogen atom is fluorine, chlorine, bromine or iodine; (ii) the optionally substituted alkyl group is $C_{1-10}$ straight-chain alkyl, $C_{3-10}$ branched-chain alkyl or $C_{3-10}$ cyclic alkyl; (iii) the optionally substituted hydroxyl group is hydroxyl, $C_{1-10}$ alkoxy, $C_{2-10}$ alkenyloxy, $C_{2-10}$ alkynyloxy, phenyl-$C_{1-4}$ alkyloxy, $C_{2-4}$ alkanoyloxy, phenoxy or 4-chlorophenoxy; (iv) the optionally substituted thiol group is thiol group, $C_{1-10}$ alkylthio, $C_{2-10}$ alkenylthio, $C_{2-10}$ alkynylthio, phenyl-$C_{1-4}$ alkylthio, $C_{2-4}$ alkanoylthio or phenylthio; (v) the optionally substituted amino group is amino group which may be substituted by $C_{1-10}$ alkyl, $C_{2-10}$ alkenyl, $C_{2-10}$ alkynyl, aromatic group, hetero cyclic group or $C_{1-10}$ acyl group; (vi) the acyl group is formyl or ones formed by bondage of $C_{1-10}$ alkyl, $C_{2-10}$ alkenyl, $C_{2-10}$ alkynyl, or an aromatic group with carbonyl group; (vii) the optionally esterified carboxyl group is a group represented by the formula —$COOR^6$, wherein $R^6$ is a hydrogen atom, $C_{1-6}$ alkyl group, aryl-$C_{1-6}$ aralkyl group or aryl group; (viii) the optionally substituted aromatic cyclic group is $C_{6-14}$ aromatic hydrocarbon group or aromatic heterocyclic group.

(10) The compound of the above item (1), wherein G is a group represented by the formula —$COOR^6$, whose $R^6$ is a hydrogen atom, $C_{1-6}$ alkyl, aryl-$C_{1-6}$alkyl or aryl.

(11) The compound of the above item (1), wherein X is —$(CH_2)_q$— (q is an integer of 0 to 3).

(12) The compound of the above item (11), wherein q is 0.

(13) The compound of the above item (1), wherein the ring A is substituted by at least one $C_{1-6}$ alkoxy.

(14) The compound of the above item (1), which is

Ethyl 6-(N,N-diethylaminomethyl)-4-(3,4-dimethoxyphenyl)-2,3-dimethylthieno[2,3-b]pyridine-5-carboxylate, 4-(3,4-Dimethoxyphenyl)-2-(N,N-diethylaminomethyl)-5,6-dimethyl-thieno[2,3-d]pyrimidine, Ethyl 2-(N,N-diethylaminomethyl)-4-(3,4-dimethoxyphenyl)-5,6-dihydro-8H-thiopyrano[4',3':4,5]thieno[2,3-b]pyridine-3-carboxylate, Ethyl 4-(3,4-dimethoxyphenyl)-5,6-dihydro-2-(1,2,4-triazol-1-ylmethyl)-8H-thiopyrano[4',3':4,5]thieno[2,3-b]pyridine-3-carboxylate, Ethyl 2-(N,N-diethylaminomethyl)-4-(3,4-dimethoxyphenyl)-5,6-dihydro-8H-pyrano[4',3':4,5]thieno[2,3-b]pyridine-3-carboxylate, Ethyl 2-(N,N-diethylaminomethyl)-4-(3,4-dimethoxyphenyl)-7-methyl-5,6,7,8-tetrahydrothieno[2,3-b:5,4-c']dipyridine-3-carboxylate, Ethyl 7-benzyl-2-(N,N-diethylaminomethyl)-4-(3,4-dimethoxyphenyl)-5,6,7,8-tetrahydrothieno[2,3-b:5,4-c']dipyridine-3-carboxylate, Ethyl 7-benzyl-4-(3,4-dimethoxyphenyl)-5,6,7,8-tetrahydro-2-(1,2,4-triazol-1-ylmethyl)thieno[2,3-b:5,4-c']dipyridine-3-carboxylate, Ethyl 7-benzyl-4-(3,5-dimethoxyphenyl)-5,6,7,8-tetrahydro-2-(1-methylimidazol-2-ylthiomethyl)thieno[2,3-b:5,4-c']dipyridine-3-carboxylate, Ethyl 2-(N,N-diethylaminomethyl)-4-(3,4-dimethoxyphenyl)-7-propyl-5,6,7,8-tetrahydrothieno[2,3-b:5,4-c']dipyridine-3-carboxylate, Ethyl 7-(4-methoxybenzyl)-4-(3,4-dimethoxyphenyl)-2-pyrrolidinomethyl-5,6,7,8-tetrahydrothieno[2,3-b:5,4-c']dipyridine-3-carboxylate.

(15) A method of producing a compound represented by the formula (I-2)

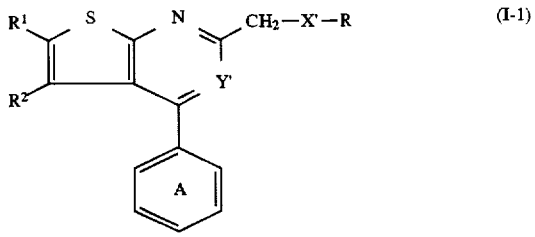  (I-1)

wherein $R^1$, $R^2$, R and ring A are of the same meaning as defined in claim 1, X' is an oxygen atom or a sulfur atom and Y' is a nitrogen atom or C-G' (G' is an esterified carboxyl group); which is characterized by allowing a compound represented by the formula (II-1)

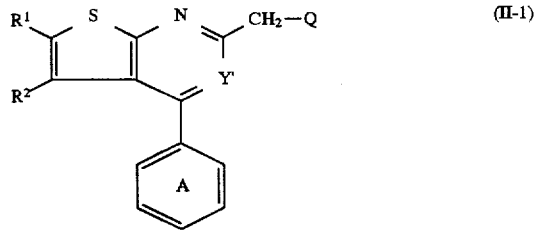  (II-1)

wherein Q is a leaving group; and other symbols are of the same meaning as defined above, to react with a compound represented by the formula (III)

R-X'H  (III)

wherein X' and R are of the same meaning as defined above.

(16) A method of producing a compound represented by the formula (I-2)

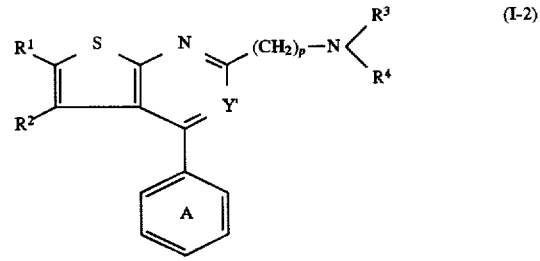  (I-2)

wherein $R^1$, $R^2$ and ring A are of the same meaning as defined in claim 1; $R^3$ and $R^4$ independently stand for a hydrogen atom, an optionally substituted hydrocarbon residue or an optionally substituted heterocyclic group, or $R^3$ and $R^4$ may be combined to form a nitrogen containing ring; Y' stands for a nitrogen atom or C-G' (G' is an esterified carboxyl group); and p is an integer of 1 to 6, which is characterized by allowing a compound represented by the formula (II-2)

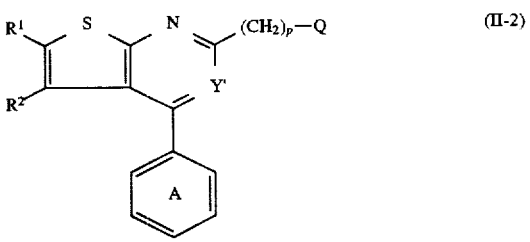  (II-2)

wherein Q is a leaving group; and other symbols are of the same meaning as defined above, to react with a compound represented by the formula (IV)

$HNR^3R^4$  (IV)

wherein $R^3$ and $R^4$ are of the same meaning as defined above.

(17) A method of producing a compound represented by the formula (I-2)

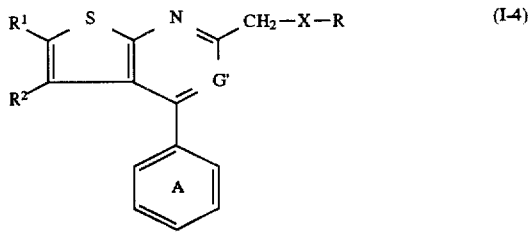  (I-4)

wherein $R^1$, $R^2$, X, R and ring A are of the same meaning as defined in claim 1; and G' is an esterified carboxyl group; which is characterized by allowing a compound represented by the formula (VIII)

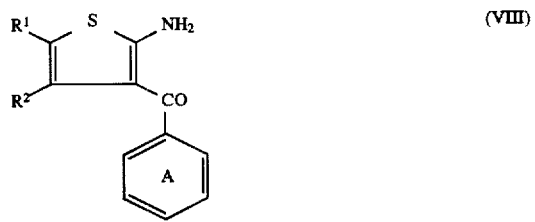  (VIII)

wherein $R^1$, $R^2$ and ring A are of the same meaning as defined above, to react with a compound represented by the formula (IX)

$R-X-CH_2COCH_2-G'$  (IX)

wherein R, X and G' are of the same meaning as defined above.

(18) A composition which comprises a compound represented by the formula (I):

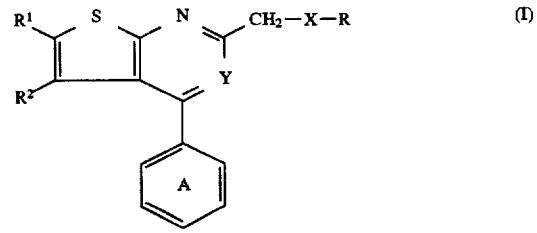  (I)

wherein $R^1$ and $R^2$ independently stand for a hydrogen atom, a halogen atom or an optionally substituted alkyl group, or $R^1$ and $R^2$ may be combined to form an optionally substituted 5- to 7-membered ring; Y is a nitrogen atom or C-G, G is an optionally esterified carboxyl group; X is an oxygen atom, an optionally oxidated sulfur atom or —(CH$_2$)$_q$— (q is an integer of 0 to 5); R is an optionally substituted heterocyclic group or an optionally substituted amino group; and ring A may optionally be substituted; or a salt thereof.

(19) The pharmaceutical composition which comprises a compound of the above item (18).

(20) The pharmaceutical composition of the above item (19), which is for the prophylaxis or treatment of an inflammatony disease.

(21) The pharmaceutical composition of the above item (19), which is for promoting anti-pyretic analgesic action.

(22) The pharmaceutical composition of the above item (19), which is for the prophylaxis or treatment of arthritis.

(23) The pharmaceutical composition of the above item (19), which is for inhibiting bone resorption.

(24) The pharmaceutical composition of the above item (19), which is for the prophylaxis or treatment of osteoporosis.

(25) The pharmaceutical composition of the above item (19), which is for supressing the production of cytokine in a mammal.

(26) A method for the prophylaxis or treatment of an inflammatony disease in a mammal which comprises administering a pharmaceutically effective amount of a compound of the above item (18) to said mammal in need thereof.

(27) A method for the prophylaxis or treatment of osteoporosis in a mammal which comprises administering a pharmaceutically effective amount of a compound of the above item (18) to said mammal in need thereof.

(28) Use of a compound of the above item (1), or a pharmaceutically acceptable salt thereof for the manufacture of a medicament to be used as an anti-inflammatory agent.

(29) Use of a compound of the above item (1), or a pharmaceutically acceptable salt thereof for the manufacture of a medicament to be used for inhibiting bone resorption.

BEST MODE FOR CARRYING OUT THE INVENTION

Various definitions included in the above-general formulae and in the scope of the present invention are hereinafter described in detail with preferable examples thereof.

In the above-mentioned formula (I), the optionally substituted amino group for R is represented by -N(R$^3$)(R$^4$), wherein R$^3$ and R$^4$ respectively stand for a hydrogen atom, an optionally substituted hydrocarbon residue or an optionally substituted heterocyclic group, or R$^3$ and R$^4$ are combined to form a nitrogen containing cyclic group.

The hydrocarbon residue in the optionally substituted hydrocarbon residue for R$^3$ or R$^4$ includes independently, for example, aliphatic hydrocarbon residues, alicyclic hydrocarbon residues, alicyclic-aliphatic hydrocarbon residues, aromatic-aliphatic hydrocarbon residues or aromatic hydrocarbon residues.

Examples of the aliphatic hydrocarbon residues include C$_{1-8}$ saturated aliphatic hydrocarbon residues (e.g., methyl, ethyl, propyl, isopropyl, butyl, isobutyl, sec-butyl, tert-butyl, pentyl, isopentyl, neopentyl, tert-pentyl, hexyl, isohexyl, heptyl, octyl); and C$_{2-8}$ unsaturated aliphatic hydrocarbon residues (e.g., ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl).

Examples of the alicyclic hydrocarbon residues include C$_{3-7}$ saturated alicyclic hydrocarbon residues (e.g., cyclopropyl, cyclobutyl, cyclopentyl, cyclohexyl, cycloheptyl); and C$_{5-7}$ unsaturated alicyclic hydrocarbon residues (e.g., 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl).

Examples of the alicyclic-aliphatic hydrocarbon residues include, among those formed by bondage of the above-mentioned alicyclic hydrocarbon residue and above-mentioned aliphatic hydrocarbon residue, C$_{4-9}$ ones such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl.

Examples of the aromatic-aliphatic hydrocarbon residues include C$_{7-9}$ phenylalkyl such as benzyl, phenethyl, 1-phenylethyl, 3-phenylpropyl, 2-phenylpropyl and 1-phenylpropyl; and C$_{11-13}$ naphtylalkyl such as α-naphthylmethyl, α-naphthylethyl, β-naphthylmethyl and β-naphthylethyl.

Examples of the aromatic hydrocarbon residues include phenyl and naphthyl (e.g., α-naphthyl, β-naphthyl, and so on).

The heterocyclic group in the optionally substituted heterocyclic group for R$^3$ or R$^4$ includes independently (i) 5- to 7-membered heterocyclic groups containing one sulfur atom, one nitrogen atom or one oxygen atom; (ii) 5- to 6-membered heterocyclic groups containing 2 to 4 nitrogen atoms; or (iii) 5- to 6-membered heterocyclic groups containing 1 to 2 nitrogen atoms and one sulfur atom or one oxygen atom. (iv) These heterocyclic groups may be condensed with a 6-membered ring containing one or two nitrogen atoms, benzene ring or a 5-membered ring containing one sulfur atom. These are exemplified by aromatic monocyclic-heterocyclic group, aromatic condensed heterocyclic group, non-aromatic heterocyclic group and so on.

Practical examples of the heterocyclic group in the optionally substituted heterocyclic group for R$^3$ or R$^4$ include independently (i) aromatic monocyclic-heterocyclic groups such as furyl, thienyl, pyrrolyl, oxazolyl, isoxazolyl, thiazolyl, isothiazolyl, imidazolyl, pyrazoly, 1,2,3-oxadiazolyl, 1,2,4-oxadiazolyl, 1,3,4-oxadiazolyl, furazanyl, 1,2,3-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl and triazinyl; (ii) aromatic condensed-heterocyclic groups such as benzofuranyl, isobenzofuranyl, benzo[b]thienyl, indolyl, isoindolyl, 1H-indazolyl, benzimidazolyl, benzoxazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,2-b]pyridazinyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl; and (iii) non-aromatic heterocyclic groups such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl.

$R^3$ and $R^4$ may, in some instances, be combined with each other to form a ring, especially nitrogen containing 5- to 7-membered ring. Examples of such -N($R^3$)($R^4$) include 1-pyrrolidinyl, 1-imidazolidinyl, 1-pyrazolidinyl, 1-piperidyl (piperidino), 1-piperazinyl, 4-morpholinyl (morpholino), 4-thiomorpholinyl, homopiperazin-1-yl, pyrazol-1-yl, imidazol-1-yl, 1,2,4-triazol-1-yl, 1,2,4-triazol-4-yl, 1,2,3-triazol-1-yl, 1,2,3-triazol-2-yl, tetrazol-1-yl, benzimidazol-1-yl, indol-1-yl and 1H-indazol-1-yl.

As the hydrocarbon residue in the optionally substituted hydrocarbon residue for $R^3$ or $R^4$, a straight- or branched-chain $C_{1-6}$, especially $C_{1-4}$, alkyl is preferable. Among them, more preferable examples include methyl, ethyl, propyl, isopropyl, butyl and so on.

Preferable examples of -N($R^3$)($R^4$), wherein $R^3$ and $R^4$ are combined each other to form a nitrogen containing ring, which includes 1,2,4-triazol-1-yl, imidazol-1-yl, morpholino, piperidino, pyrrolidino and so on.

The hydrocarbon residue and heterocyclic group for $R^3$ or $R^4$ may have 1 to 3 substituents on optionally substitutional positions of the chain or the ring thereof.

Examples of such substituents on the hydrocarbon residue and heterocyclic group for $R^3$ or $R^4$ include aliphatic hydrocarbon groups, alicyclic hydrocarbon groups, aryl group, aromatic heterocyclic group, non-aromatic heterocyclic group, halogen atoms, nitro group, optionally substituted amino group, acyl group, optionally substituted hydroxyl group, optionally substituted thiol group and optionally esterified carboxyl group.

Examples of aliphatic hydrocarbon groups as the substituent of hydrocarbon groups and heterocyclic groups for $R^3$ or $R^4$ include straight- or branched-chain aliphatic hydrocarbon group, for example, alkyl group, preferably $C_{1-10}$ alkyl group, alkenyl group, preferably $C_{2-10}$ alkenyl group, and alkynyl group, preferably $C_{2-10}$ alkynyl group. Preferable examples of the alkyl group include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl. Preferable examples of the alkenyl group include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Preferable examples of the alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 4-hexynyl and 5-hexynyl.

Examples of the alicyclic hydrocarbon group as the substituent of hydrocarbon residue and heterocyclic group for $R^3$ or $R^4$ include saturated or unsaturated $C_{3-8}$ alicyclic hydrocarbon groups such as $C_{3-8}$ cycloalkyl group, $C_{3-8}$ cycloalkenyl group and $C_{4-8}$ cycloalkadienyl group. Preferable examples of the $C_{3-8}$ cycloalkyl group include cyclopropyl, cyclobutyl, cyclopentyl, cyclohexyl, cycloheptyl, cyclooctyl, bicyclo[2.2.1]heptyl, bicyclo[2.2.2]octyl and bicyclo[3.2.1]octyl. Preferable examples of the $C_3$-cycloalkenyl group include 2-cyclopenten-1-yl, 3-cyclopenten-1-yl, 2-cyclohexen-1-yl and 3-cyclohexen-1-yl. Preferable examples of the $C_{4-8}$ cycloalkadienyl group include 2,4-cyclopentadien-1-yl, 2,4-cyclohexadien-1-yl and 2,5-cyclohexadien-1-yl.

The aryl group as the substituent on the hydrocarbon residue and heterocyclic group for $R^3$ or $R^4$ is a monocyclic or condensed-polycyclic aromatic hydrocarbon group. Preferable examples of it include phenyl, naphthyl, anthryl, phenanthryl and acenaphthylenyl. Among them, phenyl, 1-naphthyl and 2-naphthyl are more preferable.

Preferable examples of the aromatic heterocyclic group as the substituent of the hydrocarbon residue and heterocyclic group for $R^3$ or $R^4$ include aromatic monocyclic-heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl; and aromatic condensed-heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo [1,2-a]pyridyl, imidazo[1,5-a]pyridyl, imidazo[1,2-b] pyridazinyl, imidazo[1,2-a]pyrimidinyl, 1,2,4-triazolo[4,3-a]pyridyl and 1,2,4-triazolo[4,3-b]pyridazinyl.

Preferable examples of the non-aromatic heterocyclic group as the substituent of the hydrocarbon residue and heterocyclic group for $R^3$ or $R^4$ include oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl.

Examples of the halogen atom as the substituent of the hydrocarbon residue and heterocyclic group for $R^3$ or $R^4$ include fluorine, chlorine, bromine and iodine. Among them, fluorine and chlorine are especially preferable.

Examples of the optionally substituted amino group as the substituent of the hydrocarbon residue and heterocyclic group for $R^3$ or $R^4$ include, in addition to amino group, substituted amino groups, for example, amino groups having one or two of $C_{1-10}$ alkyl groups, $C_{2-10}$ alkenyl groups, $C_{2-10}$ alkynyl groups, aromatic groups, heterocyclic groups or $C_{1-10}$ acyl groups, (e.g., methylamino, dimethylamino, ethylamino, diethylamino, dibutylamino, diallylamino, cyclohexylamino, phenylamino, N-methyl-N-phenylamino, acetylamino, propionylamino, benzoylamino, nicotinoylamino).

Examples of the acyl group as the substituent of the hydrocarbon residue and heterocyclic group for $R^3$ or $R^4$ include formyl or groups formed by binding of a $C_{1-10}$ alkyl group, $C_{2-10}$ alkenyl group, $C_{2-10}$ alkynyl group or aromatic group with carbonyl group, (e.g., acetyl, propionyl, butyryl, isobutyryl, valeryl, isovaleryl, pivaloyl, hexanoyl, heptanoyl, octanoyl, cyclobutancarbonyl, cyclopentanecarbonyl, cyclohexanecarbonyl, cycloheptanecarbonyl, crotonyl, 2-cyclohexenecarbonyl, benzoyl, nicotinoyl).

Examples of the optionally substituted hydroxyl group as the substituent of the hydrocarbon residue and heterocyclic group for $R^3$ or $R^4$ include hydroxyl group and hydroxyl groups having an appropriate substituent, especially a group which is used as a hydroxyl-protecting group, as exemplified by, alkoxy, alkenyloxy, alkynyloxy, aralkyloxy, acyloxy, aryloxy and so on.

Preferable examples of the alkoxy group include $C_{1-10}$ alkoxy groups (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy, cyclohexyloxy).

Preferable examples of the alkenyloxy group include $C_{2-10}$ alkenyloxy groups (e.g., allyloxy, crotyloxy, 2-pentenyloxy, 3-hexenyloxy, 2-cyclopentenylmethoxy, 2-cyclohexenylmethoxy).

Preferable examples of the alkynyloxy group include $C_{2-10}$ alkynyloxy groups (e.g., ethynyloxy, 2-propynyloxy, etc.).

Preferable examples of the aralkyloxy group include phenyl-$C_{1-4}$ alkyloxy groups (e.g., benzyloxy, phenethyloxy).

Preferable examples of the acyloxy group include $C_{2-4}$ alkanoyloxy groups (e.g., acetyloxy, propionyloxy, butyryloxy, isobutyryloxy), $C_{3-4}$ alkenoyloxy groups and $C_{3-4}$ alkynoyloxy groups.

Preferable examples of the aryloxy group include phenoxy, 4-chlorophenoxy and so on.

Examples of the optionally substituted thiol group as the substituent of the hydrocarbon residue and heterocyclic group for $R^3$ or $R^4$ include thiol group and thiol groups having an appropriate substituent, especially a group which is used as a thiol-protecting group, as exemplified by alkylthio, alkenylthio, alkynylthio, aralkylthio, acylthio, arylthio and so on.

Preferable examples of the alkylthio group include $C_{1-10}$ alkylthio groups (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio).

Preferable examples of the alkenylthio group include $C_{2-10}$ alkenylthio groups (e.g., allylthio, crotylthio, 2-pentenylthio, 3-hexenylthio, 2-cyclopentenylmethylthio, 2-cyclohexenylmethylthio).

Preferable examples of the alkynylthio group include $C_{2-10}$ alkynylthio groups (e.g., ethynylthio, 2-propynylthio, etc.).

Examples of the aralkylthio group include phenyl-$C_{1-4}$ alkylthio groups (e.g., benzylthio, phenethylthio and so on).

Preferable examples of the acylthio group include $C_{2-4}$ alkanoylthio groups (e.g., acetylthio, propionylthio, butyrylthio, isobutyrylthio).

Preferable examples of the arylthio group include phenylthio, 4-chlorophenylthio and so on.

Examples of the optionally esterified carboxyl group as the substituent of the hydrocarbon residue and heterocyclic group for $R^3$ or $R^4$ include, in addition to carboxyl group, alkyloxycarbonyl group, alkenyloxycarbonyl group, alkynyloxycarbonyl group, aralkyloxycarbonyl group, acyloxycarbonyl group and aryloxycarbonyl group.

Examples of the alkyl group in the alkyloxycarbonyl group include $C_{1-6}$ alkyl group (e.g., methyl, ethyl, propyl, isopropyl, butyl, isobutyl, sec-butyl, tert-butyl).

Examples of the alkenyl group in the alkenyloxycarbonyl group include $C_{2-6}$ alkenyl group (e.g., vinyl, allyl, 1-propenyl, isopropenyl, 1-butenyl, 2-butenyl, 2-methylallyl).

Examples of the alkynyl group in the alkynyloxycarbonyl group include $C_{2-6}$ alkynyl group (e.g., ethynyl, 2-propynyl).

Examples of the aralkyl group in the aralkyloxycarbonyl group means an aryl-alkyl group. As the aryl group, for example, phenyl or naphthyl is preferable, which may optionally have similar substituents as those which the aryl group, exemplified as the hydrocarbon group shown by $R^3$ or $R^4$, may optionally have. As the alkyl group, $C_{1-6}$ lower alkyl groups (e.g., methyl, ethyl, propyl, butyl and so on) are preferable. Preferable examples of the aralkyl group include benzyl, phenethyl, 3-phenylpropyl, (1-naphthyl)methyl and (2-naphthyl)methyl, and, among them, benzyl and phenethyl are preferable.

Examples of the acyl group in the acyloxycarbonyl group include formyl, $C_{2-4}$ alkanoyl, $C_{3-4}$ alkenoyl, $C_{3-4}$ alkynoyl and so on.

Examples of the aryl group in the aryloxycarbonyl group include phenyl, naphytyl and so on.

The substituent on the hydrocarbon residue and heterocyclic group for $R^3$ or $R^4$ may optionally have further one or more, preferably 1 to 3, substituents on appropriate positions. As the substituents, mention is made of similar ones shown as the substituents on the hydrocarbon residue and heterocyclic group for $R^3$ or $R^4$, as exemplified by a $C_{1-10}$ lower alkyl group, a $C_{2-10}$ lower alkenyl group, a $C_{2-10}$ lower alkynyl group, $C_{3-7}$ cycloalkyl group, $C_{3-7}$ cycloalkenyl group, $C_{4-8}$ cycloalkadienyl group, aryl group, aromatic heterocyclic group, non-aromatic heterocyclic group, aralkyl group (e.g., aryl-$C_{1-6}$ alkyl), amino group, an N-mono-substituted amino group, an N,N-disubstituted amino group, amidino group, acyl group, carbamoyl group, an N-monosubstituted carbamoyl group (e.g., methylcarbamoyl, ethylcarbamoyl, phenylcarbamoyl), an N,N-disubstituted carbamoyl group (e.g., N,N-dimethylcarbamoyl, N,N-diethylcarbamoyl, piperidinocarbamoyl, morpholinocarbamoyl, etc.), sulfamoyl group, an N-monosubstituted sulfamoyl group (e.g., methylsulfamoyl, ethylsulfamoyl, phenylsulfamoyl, p-toluenesulfamoyl), an N,N-disubstituted sulfamoyl group (e.g., N,N-dimethylsulfamoyl, N-methyl-N-phenylsulfamoyl, piperidinosulfamoyl, morpholinosulfamoyl, etc.), carboxyl group, a lower $C_{1-10}$ alkoxycarbonyl group (e.g., methoxycarbonyl, ethoxycarbonyl, isopropoxycarbonyl, sec-butoxycarbonyl, isobutoxycarbonyl, tert-butoxycarbonyl), hydroxyl group, a lower $C_{1-10}$ alkoxy group, a lower $C_{2-10}$ alkenyloxy group, $C_{3-7}$ cycloalkyloxy group, aralkyloxy group, aryloxy group, mercapto group, a lower $C_{1-10}$ alkylthio group, aralkylthio group, arylthio group, sulfo group, cyano group, azido group, nitro group, nitroso group, halogen and so on.

In the above-mentioned formula (I), the heterocyclic group in the optionally substituted heterocyclic group for R is, for example, similar ones to those defined above in reference to $R^3$ or $R^4$.

The heterocyclic group in the optionally substituted heterocyclic group for R are exemplified by (i) 5- to 7-membered heterocyclic groups containing one sulfur atom, one nitrogen atom or one oxygen atom; (ii) 5- to 6-membered heterocyclic groups containing 2 to 4 nitrogen atoms; (iii) 5- to 6-membered heterocyclic groups containing 1 to 2 nitrogen atoms and one sulfur atom or one oxygen atom; or (iv) groups formed by condensation of such group with a 6-membered group containing two or less nitrogen atom, benzene ring or a 5-membered ring containing one sulfur atom.

These heterocyclic groups may have 1 to 3 substituents at optionally substitutional positions of the ring. As such substituents, mention is made of similar ones shown as the substituents on the hydrocarbon residue or heterocyclic group for $R^3$ or $R^4$. These are exemplified by $C_{1-10}$ aliphatic hydrocarbon groups, $C_{3-7}$ alicyclic hydrocarbon groups, aryl group, aromatic heterocyclic groups, non-aromatic heterocyclic groups, halogen atom, nitro group, optionally substituted amino group, acyl group, optionally substituted hydroxyl group, optionally substituted thiol group, optionally esterified carboxyl group and so on.

These substituents on the heterocyclic group may optionally have further one or more, preferably 1 to 3, substituents on appropriate positions. As these substituents, mention is made of similar ones as shown above, namely, a $C_{1-10}$ lower alkyl group, a $C_{2-10}$ lower alkenyl group, a $C_{2-10}$ lower alkynyl group, $C_{3-7}$ cycloalkyl group, $C_{3-7}$ cycloalkenyl group, $C_{4-8}$ cycloalkadienyl group, aryl group, an aromatic heterocyclic group, a non-aromatic heterocyclic group, aralkyl group (e.g., aryl-$C_{1-6}$ alkyl), amino group, an N-mono-substituted amino group, an N,N-disubstituted amino group, amidino group, acyl group, carbamoyl group, an N-mono-substituted carbamoyl group, an N,N-disubstituted carbamoyl group, sulfamoyl group, an N-monosubstituted sulfamoyl group, an N,N-disubstituted sulfamoyl group, carboxyl group, a lower $C_{1-10}$ alkoxycarbonyl group, hydroxyl group, a lower $C_{1-10}$ alkoxy group, a lower $C_{2-10}$ alkenyloxy group, $C_{3-7}$ cycloalkyloxy group, aralkyloxy group, aryloxy group, mercapto group, a lower $C_{1-10}$ alkylthio group, aralkylthio group, arylthio group, sulfo group, cyano group, azido group, nitro group, nitroso group, halogen and so on.

Preferable examples of the heterocyclic group in the optionally substituted heterocyclic group for R include 1-pyrrolidinyl, 1-imidazolidinyl, 1-pyrazolidinyl, 1-piperidyl (piperidino), 1-piperazinyl, 4-morpholinyl (morpholino), 4-thiomorpholinyl, homopiperazin-1-yl, pyrazol-1-yl, imidazol-1-yl, 1,2,4-triazol-1-yl, 1,2,4-triazol-4-yl, 1,2,3-triazol-1-yl, 1,2,3-triazol-2-yl, tetrazol-1-yl, benzimidazol-1-yl, indol-1-yl and 1H-indazol-1-yl, especially, 1,2,4-triazol-1-yl, imidazol-1-yl, morpholino, piperidino, pyrrolidino and so on.

In the above formula (I), examples of the halogen atoms for $R^1$ or $R^2$ include fluorine, chlorine, bromine and iodine. Among them, fluorine and chlorine are preferable.

In the above formula (I), examples of the alkyl group in the optionally substituted alkyl group for $R^1$ or $R^2$ include straight-chain $C_{1-6}$ alkyl or branched-chain $C_{3-6}$ alkyl groups such as methyl, ethyl, propyl, isopropyl, butyl, isobutyl, sec-butyl, tert-butyl, pentyl, isopentyl, sec-pentyl, hexyl, expecially methyl, ethyl propyl and so on.

In the above formula (I), as the substituent of the optionally substituted alkyl groups for $R^1$ or $R^2$, mention is made of aliphatic chain hydrocarbon groups, alicyclic hydrocarbon groups, aryl group, aromatic heterocyclic groups, non-aromatic heterocyclic groups, halogen atoms, nitro group, optionally substituted amino group, acyl group, optionally substituted hydroxyl group, optionally substituted thiol group, optionally esterified or amidated carboxyl group and so on. As such aliphatic chain hydrocarbon groups, alicyclic hydrocarbon groups, aryl group, aromatic, heterocyclic groups, non-aromatic heterocyclic groups, halogen atoms, nitro group, optionally substituted amino group, acyl group, optionally substituted hydroxyl group, optionally substituted thiol group and optionally esterified carboxyl group, mention is made of such ones as similar to those exemplified as the substituents on the hydrocarbon residue or heterocyclic group shown by the above $R^3$ and $R^4$. As the amidated carboxyl group, mention is made of ones represented by -CON($R^3$)($R^4$), wherein $R^3$ and $R^4$ are of the same meaning as defined above.

Or, $R^1$ and $R^2$ may be combined with each other to form a 5- to 7-membered ring formed together with the carbon atoms on the thiophene ring. The 5- to 7-membered ring comprising $R^1$ and $R^2$ is (i) $C_{5-7}$ alicyclic hydrocarbon groups, or (ii) heterocyclic group containing one to 4 oxygen atom, one to 4 sulfur atom which may be oxidized, or one nitrogen atom which may be substituted by $C_{1-10}$ alkyl, preferably $C_{1-4}$ alkyl which may be substituted. The 5- to 7-membered ring is represented by the formula of —$R^1$—$R^2$—, which is for example, —$(CH_2)_3$—, —$(CH_2)_4$—, —$(CH_2)_5$—, —$CH_2$—N($R^5$)—$CH_2$—$CH_2$e— ($R^5$ stands for a $C_{1-4}$ alkyl group which may be substituted by phenyl), —$CH_2$—S—$CH_2$—$CH_2$—, —$CH_2$—SO—$CH_2$—$CH_2$—, —$CH_2$—$SO_2$—$CH_2$—$CH_2$—, or —$CH_2$—O—$CH_2$—$CH_2$—, preferably, —$CH_2N(R^5)$—$CH_2$—$CH_2$— ($R^5$ stands for methyl, ethyl, propyl, benzyl etc.). The $C_{1-4}$ alkyl group for $R^5$ may have a phenyl group which may be substituted at optionally substitutional positions of the chain.

The phenyl group on the $C_{1-4}$ alkyl group for $R^5$ may optionally have one or more, preferably 1 to 3, substituents on its substitutional positions. As the substituents, mention is made of similar ones shown as the substituents on the hydrocarbon residue and heterocyclic group for $R^3$ or $R^4$, as exemplified by a $C_{1-10}$ lower alkyl group, a $C_{2-10}$ lower alkenyl group, a $C_{2-10}$ lower alkynyl group, $C_{3-7}$ cycloalkyl group, $C_{3-7}$ cycloalkenyl group, $C_{4-8}$ cycloalkadienyl group, aryl group, aromatic heterocyclic group, non-aromatic heterocyclic group, aralkyl group (e.g., aryl-$C_{1-6}$ alkyl), amino group, an N-mono-substituted amino group, an N,N-di-substituted amino group, amidino group, acyl group, carbamoyl group, an N-mono-substituted carbamoyl group (e.g., methylcarbamoyl, ethylcarbamoyl, phenylcarbamoyl), an N,N-di-substituted carbamoyl group (e.g., N,N-dimethylcarbamoyl, N,N-diethylcarbamoyl, piperidinocarbamoyl, morpholinocarbamoyl, etc.), sulfamoyl group, an N-mono-substituted sulfamoyl group (e.g., methylsulfamoyl, ethylsulfamoyl, phenylsulfamoyl, p-toluenesulfamoyl), an N,N-disubstituted sulfamoyl group (e.g., N,N-dimethylsulfamoyl, N-methyl-N-phenylsulfamoyl, piperidinosulfamoyl, morpholinosulfamoyl, etc.), carboxyl group, a lower $C_{1-10}$ alkoxycarbonyl group (e.g., methoxycarbonyl, ethoxycarbonyl, isopropoxycarbonyl, sec-butoxycarbonyl, isobutoxycarbonyl, tert-butoxycarbonyl), hydroxyl group, a lower $C_{1-10}$ alkoxy group, a lower $C_{2-10}$ alkenyloxy group, $C_{3-7}$ cycloalkyloxy group, aralkyloxy group, aryloxy group, mercapto group, a lower $C_{1-10}$ alkylthio group, aralkylthio group, arylthio group, sulfo group, cyano group, azido group, nitro group, nitroso group, halogen and so on.

$R^5$ is preferably $C_{1-3}$ alkyl (especially, methyl, ethyl, propyl, isopropyl etc.), or phenyl $C_{1-3}$ alkyl (especially, benzyl, phenetyl, 4-methoxybenzyl, etc.).

Preferable examples of optionally substituted 5- to 7-membered ring (—$R^1$—$R^2$—) include —$CH_2$—N($CH_3$) —$CH_2$-$CH_2$—,

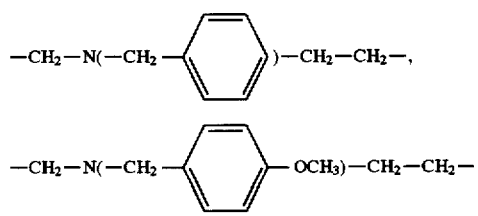

and so on.

In the above-mentioned formula (I), Y is a nitrogen atom or C-G, wherein G is an optionally esterified carboxyl group.

The optionally esterified carboxyl group is represented by the formula —COOR$^6$ (R$^6$ is a hydrogen atom, alkyl group, aralkyl group or aryl group).

As the alkyl group for R$^6$, mention is made of C$_{1-6}$ alkyl groups such as methyl ethyl, propyl, isopropyl, butyl, isobutyl, sec-butyl and tert-butyl. The aralkyl group for R$^6$ means the alkyl group having aryl group as the substituent (e.g., aryl-C$_{1-6}$ alkyl group). Examples of the aryl group include phenyl, naphthyl and so on. The aralkyl group for R$^6$ includes, for example, benzyl, phenethyl, 3-phenylpropyl, (1-naphthyl)methyl and (2-naphthyl)methyl. As the aryl group for R$^6$, mention is made of, for example, phenyl and naphthyl.

Preferable examples of Y is C—COOR$^6$ (R$^6$ is C$_{1-4}$ alkyl), more preferably C—COOC$_2$H$_5$.

In the above-mentioned formula (I), X is an oxygen atom, an optionally oxidized sulfur atom or —(CH$_2$)$_q$—, wherein q is an integer of 0 to 5, preferably an integer of 0 to 3.

The optionally oxidized sulfur atom for X is thio group, sulfinyl group or sulfonyl group. Among them, thio group is preferable. The group —(CH$_2$)$_q$— (wherein q is 0) represented by X is more preferable.

In the formula (I), the ring A may optionally have a substituent, as exemplified by a halogen atom, nitro group, an optionally substituted alkyl group, an optionally substituted hydroxyl group, an optionally substituted thiol group, an optionally substituted amino group, an acyl group, an optionally esterified carboxyl group, an optionally substituted aromatic cyclic group and so on.

Examples of the halogen atom as the substituent on the ring A include fluorine, chlorine, bromine and iodine. Among them, fluorine and chlorine are especially preferable.

Examples of the optionally substituted alkyl group as the substituent on the ring A include C$_{1-10}$ straight-chain alkyl group, C$_{3-10}$ branched-chain alkyl group or C$_{3-10}$ cyclic alkyl group, as exemplified by methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclobutyl, cyclopentyl, cyclohexyl, cycloheptyl and so on. Examples of the optionally substituted hydroxyl group as the substituent of the ring A include hydroxyl group and a hydroxyl group having an appropriate substituent, especially a group which is used as a hydroxyl-protecting group, such as, alkoxy, alkenyloxy, alkynyloxy, aralkyloxy, acyloxy and aryloxy. Preferable examples of the alkoxy include C$_{1-10}$ alkoxy (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy, coclohexyloxy). Preferable examples of the alkenyloxy include C$_{2-10}$ alkenyloxy (e.g., allyloxy, crotyloxy, 2-pentenyloxy, 3-hexenyloxy, 2-cyclopentenylmethoxy, 2-cyclohexenylmethoxy). Preferable examples of the alkynyloxy include C$_{2-10}$ alkynyloxy (e.g., ethynyloxy, 2-propynyloxy, etc.). Preferable examples of the aralkyloxy include, for example, phenyl-C$_{1-4}$ alkyloxy (e.g., benzyloxy phenethyloxy, and so on). Preferable examples of the acyloxy include C$_{2-4}$ alkanoyloxy (e.g., acetyloxy, propionyloxy, butyryloxy, isobutyryloxy, and so on). Preferable examples of the aryloxy include phenoxy, 4-chlorophenoxy and so on.

Examples of the optionally substituted thiol group as the substituent on the ring A include a thiol group and a thiol group having an appropriate substituent, especially a thiol-protecting group, such as alkylthio, alkenylthine, alkynylthio, aralkylthio, acylthio and arylthio. Preferable examples of the alkylthio include C$_{1-}$ alkylthio (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio). Preferable examples of the alkenylthio include C$_{2-10}$ alkenylthio (e.g., allylthio, crotylthio, 2-pentenylthio, 3-hexenylthio, 2-cyclopentenylmethylthio, 2-cyclohexenylmethylthio, etc.). Preferable examples of the alkynylthio include C$_{2-10}$ alkynylthio (e.g., ethynylthio, 2-propynylthio, etc.). Preferable examples of the aralkylthio include phenyl-C$_{1-4}$ alkylthio (e.g., benzylthio, phenethylthio and so on). Preferable examples of the acylthio include C$_{2-4}$ alkanoylthio (e.g., acetylthio, propionylthio, butyrylthio, isobutyrylthio and so on). Preferable examples of the arylthio include phenylthio, 4-chlorophenylthio and so on.

Examples of the optionally substituted amino group as the substituent on the ring A include, in addition to amino group, substituted amino groups, for example, amino groups having one or two C$_{1-10}$ alkyl, C$_{2-10}$ alkenyl, C$_{2-10}$ alkynyl, aromatic groups, heterocyclic groups or C$_{1-10}$ acyl groups (e.g., methylamino, dimethylamino, ethylamino, diethylamino, dibutylamino, diallylamino, cyclohexylamino, phenylamino, N-methyl-N-phenylamino, acetylamino, propionylamino, benzoylamino, nicotinylamino, and so on).

Examples of the acyl as the substituent on the ring A include formyl or the acyl groups formed by bondage of C$_{1-10}$ alkyl, C$_{2-10}$ alkenyl, C$_{2-10}$ alkynyl group or an aromatic group with carbonyl group (e.g., acetyl, propionyl, butyryl, isobutyryl, valeryl, isovaleryl, pivaloyl, hexanoyl, heptenoyl, octanoyl, cyclobutanecarbonyl, cyclopentanecarbonyl, cyclohexanecarbonyl, cycloheptanecarbonyl, crotonyl, 2-hexanecarbonyl, benzoyl, nicotinoyl and so on).

Examples of the optionally esterified carboxyl group as the substituent on the ring A include, in addition to carboxyl group, alkyloxycarbonyl group alkenyloxycarbonyl group, alkynyloxycarbonyl group, aralkyloxycarbonyl group, acyloxycarbonyl group and aryloxycarbonyl group. These groups are represented by the formula —COOR$^6$ (R$^6$ is a hydrogen atom, C$_{1-6}$ alkyl group, aryl-C$_{1-6}$ alkyl group or aryl group). Preferable examples of the alkyl group in the alkyloxycarbonyl group include C$_{1-6}$ alkyl groups such as methyl, ethyl, propyl, isopropyl, butyl, isobutyl, sec-butyl and tert-butyl. Preferable examples of the aralkyl group in the aralkyloxycarbonyl group means aryl-alkyl group. As the aryl group, for example, phenyl or naphthyl is preferable, which may optionally have similar substituents as those which the aryl group, as exemplified as the hydrocarbon for R$^3$ or R$^4$, may optionally have. As the alkyl group, C$_{1-6}$ lower alkyl groups (e.g., methyl, ethyl, propyl, butyl, etc.) are preferable. Preferable examples of the aralkyl group include benzyl, phenethyl, 3-phenylpropyl, (1-naphthyl) methyl and (2-naphthyl)methyl, and, among them, benzyl and phenethyl are more preferable.

Examples of the optionally substituted aromatic cyclic group as the substituent on the ring A include, in addition to C$_{6-14}$ aromatic hydrocarbon groups (e.g., phenyl, naphthyl, anthryl, etc.), aromatic heterocyclic groups (e.g., pyridyl, furyl, thienyl, imidazolyl, thiazolyl, etc.).

Such substituents on the ring A mentioned above may occupy any substitutional position on the ring. The substituent on the ring A is placed, preferably, at 3- and/or 4-position of the ring A. These substituents may be the same as or different from one another, and the number ranges from 1 to 4, preferably 1 or 2. When the substituents on the ring A are adjacent to each other, the adjacent groups may be combined to form a ring shown by —(CH$_2$)$_m$— or —O—(CH$_2$)$_l$—O—, wherein m denotes an integer of 3 to 5, and l denotes an integer of 1 to 3, and these rings include 5- to 7-membered ring formed together with the carbon atoms on the benzene ring.

Preferably, the ring A is substituted with at least one C$_{1-6}$ alkoxy group, preferably C$_{1-3}$ alkoxy group, more preferably at least one methoxy group; or the same or different two C$_{1-3}$ alkoxy groups, preferably two methoxy groups. More preferably, the ring A is substituted with two methoxy groups at the 3- and 4-positions of the ring A.

In particular, the compound of the formula (I) is preferably that wherein both R$^1$ and R$_2$ are methyl, or R$^1$ and R$^2$ are combined with each other to form 6-membered nitrogen containing ring in which —R$^1$—R$^2$— is —CH$_2$—N(R$^5$)—CH$_2$—CH$_2$— (R$^5$ is C$_{1-3}$ alkyl or benzyl), Y is C-G in which G is ethoxycabonyl, -X-R is N,N-diethylamino, 1,2,4-triazol-1-yl, 1-methyl-imidazol-2-ylthio or pyrrolidino, the ring A is substituted with methoxy groups at the 3- and 4-positions of it.

The salt of the object compound of the present invention is preferably a pharmaceutically acceptable salt, exemplified by salts with inorganic bases, salts with organic bases, salts with inorganic acids, salts of organic acids and salts with basic or acidic amino acid. Preferable examples of salts with an inorganic base include alkali metal salts such as sodium salt and potassium salt; alkaline earth metal salts such as calcium salt and magnesium salt; and aluminum salt and ammonium salt. Preferable examples of salts with an organic base include salts with triemthylamine, triethylamine, pyridine, picoline, ethanolamine, diethanolamine, triethanolamine, dicyclohexylamine and N,N'-dibenzylethylenediamine. Preferable examples of salts with an inorganic acid include salts with hydrochloric acid, hydrobromic acid, nitric acid, sulfuric acid and phosphoric acid. Preferable examples of salts with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable examples of salts with a basic amino acid include salts with arginine, lysine and ornithine, while preferable examples with an acidic amino acid include salts with aspartic acid and glutamic acid.

The object compound (I) of this invention can be administered orally or non-orally, along with a pharmaceutically acceptable carrier, in the form of solid preparations such as tablets, capsules, granules and powders, or liquid preparations such as syrups and injections.

As pharmaceutically acceptable carriers, use is made of various organic or inorganic carriers in common use as pharmaceutical materials, including excipients, lubricants, binders and disintegrants for solid preparations; and solvents, solubilizers, suspending agents, isotonizers, buffers and soothing agents for liquid preparations. Other pharmaceutical additives such as preservatives, antioxidants, coloring agent and sweeteners may be used as necessary.

Preferable excipients are, for example, lactose, sucrose, D-mannitol, starch, crystalline cellulose and light silicon dioxide.

Preferable lubricants are, for example, magnesium stearate, calcium stearate, talc and colloidal silica.

Preferable binders are, for example, binding cellulose, sucrose, D-mannitol, dextrin, hydroxypropyl cellulose, hydroxypropyl methyl cellulose and polyvinyl-pyrrolidone.

Preferable disintegrators are, for example, starch, carboxymethyl cellulose, carboxymethyl cellulose calcium, cross carmellose sodium and carboxymethyl starch sodium.

Preferable solvents are, for example, water for injection, alcohol, propylene glycol, macrogol, sesame oil and corn oil.

Preferable solubilizers are, for example, polyethylene glycol, D-mannitol, benzyl benzoate, ethanol, trisaminomethane, cholesterol, triethanolamine, sodium carbonate and sodium citrate.

Preferable suspending agent include, for example, surfactants such as stearyl triethanolamine, sodium lauryl sulfate, lauryl aminopropionic acid, lecithin, benzalkonium chloride, benzethonium chloride and monostearic glycerol; and hydrophilic polymers such as polyvinyl alcohol, polyvinyl pyrrolidone, carboxymethyl cellulose sodium, methyl cellulose, hydroxymethyl cellulose, hydroxyethyl cellulose and hydroxypropyl cellulose.

Preferable isotonizers are, for example, sodium chloride, glycerol and D-mannitol.

Preferable buffers are, for example, phosphate, acetate, carbonate and citrate buffer solutions.

Preferable soothing agents are, for example, benzyl alcohol.

Preferable preservatives are, for example, p-oxybenzoic acid esters, chlorobutanol, benzyl alcohol, phenethyl alcohol, dehydroacetic acid and sorbic acid.

Preferable antioxidants are, for example, sulfites and ascorbic acid.

The above-mentioned compound (I) can be produced by, for example, the following methods, namely:

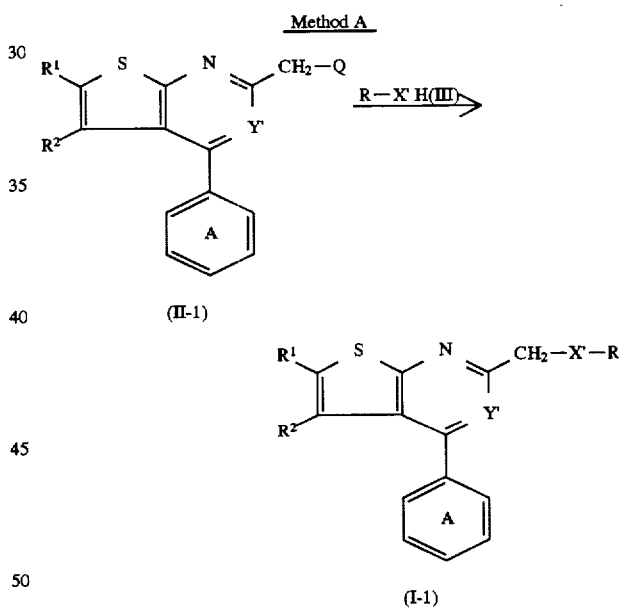

[wherein Q stands for a leaving group; Y' stands for Nitrogen atom or C-G'; G' stands for an esterified carboxyl group; X' stands for oxygen atom or sulfur atom; and other symbols are of the same meaning as defined above].

In the general formula (II-1), examples of the leaving group shown by Q include halogen, preferably chlorine, bromine or iodine; hydroxyl group activated by esterification, such as a residual group of an organic sulfonic acid (e.g., p-toluenesulfonyloxy group and methanesulfonyloxy group) or a residual group of an organic phosphoric acid, such as diphenylphosphoryloxy group, dibenzylphosphoryloxy group and dimethylphosphoryloxy group; and examples of the esterified carboxyl group shown by G' include groups similar to those exemplified as the esterified carboxyl group shown by G.

In this method, (II-1) is allowed to react with (III) in the presence of a base to produce (I-1). The reaction of (II-1) with (III) is conducted in a proper solvent. Examples of the solvent include aromatic hydrocarbon such as benzene, toluene and xylene; ethers such as dioxane, tetrahydrofuran and dimethoxyethane; alcohols such as methanol, ethanol and propanol; ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and a mixture of these solvents. The reaction of (II-1) with (III) is conducted in the presence of a proper base, for example, an alkali metal salt such as sodium hydroxide, potassium hydroxide, sodium carbonate and sodium hydrogencarbonate; silver carbonate ($Ag_2CO_3$), sodium hydride and potassium hydride; and amines such as pyridine, triethylamine, N,N-dimethylaniline, 1,5-diazabicyclo[4.3.0]non-5-ene, 1,4-diazabicyclo[2.2.2]octane and 1,8-diazabicyclo[5.4.0]undec-7-ene. The amount of these bases to be employed ranges preferably from about 1 to about 5 molar equivalents relative to (II-1). This reaction conducted at temperature usually ranging from −20° C. to 150° C., preferably from about −10° C. to 100° C. The thienopyridine or thienopyrimidine derivative (I-1) thus obtained can be isolated and purified by a conventional separating and purifying means such as concentration, concentration under reduced pressure, solvent-extraction, crystallization, recrystallization, phasic transfer and chromatography.

Method B

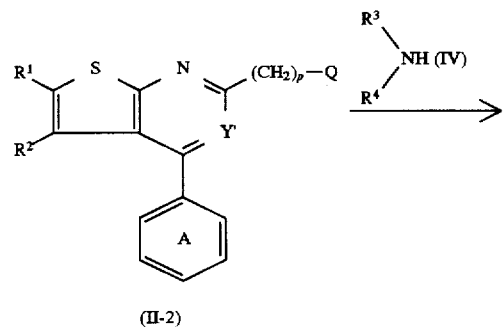

(II-2)

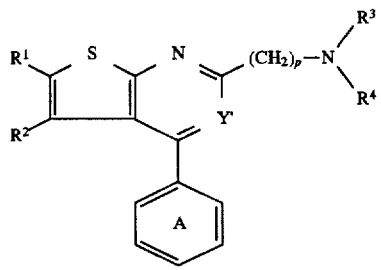

(I-2)

[wherein p denotes an integral number of 1 to 6, and other symbols are of the same meaning as defined above].

In this method, (II-2) is allowed to react with (IV) in the presence of a base to produce (I-2). The reaction of (II-2) with (IV) is conducted in an adequate solvent. Examples of the solvent include aromatic solvent such as benzene, toluene and xylene; ethers such as dioxane, tetrahydrofuran and dimethoxyethane; alcohols such as methanol, ethanol and propanol; ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone and 2-butanone; and a mixture of these solvents. The reaction of (II-2) with (IV) is conducted in the presence of an adequate base, as exemplified by an alkali metal salt such as sodium hydroxide, potassium hydroxide, potassium carbonate, sodium carbonate and sodium hydrogencarbonate; amines such as pyridine, triethylamine and N,N-dimethylaniline; sodium hydride or potassium hydride. The amount of these bases to be employed is preferably in a range from about 1 to about 5 molar equivalents relative to the compound (II-2). This reaction is conducted at temperature usually ranging from −20° C. to 150° C., preferably from about −10° C. to 100° C. This reaction can be conducted also by using an excess amount of (IV) as the base.

The thienopyridine or thienopyrimidine derivative (I-2) can be isolated and purified by a conventional separating and purifying means, for example, concentration, concentration under reduced pressure, solvent-extraction, crystallization, recrystallization, phasic transfer and chromatography.

Method C

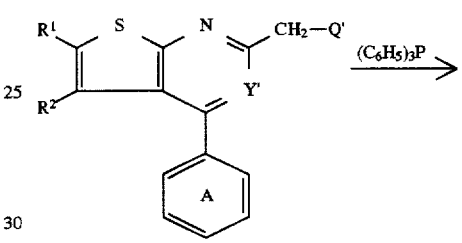

(II-3)

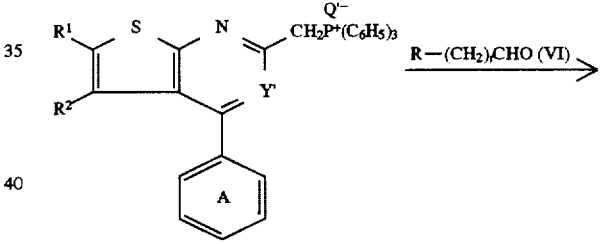

(V)

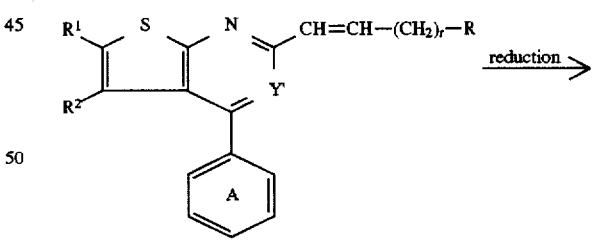

(VII)

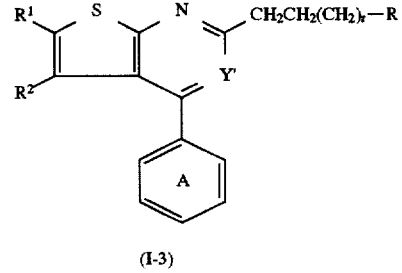

(I-3)

[in formulas (II-3) and (V), Q' stands for a halogen atom; in formulas (VI), (VII), and (I-3), t denotes an integer of 0 to 4; other symbols are of the same meaning as defined above].

As the halogen atom shown by Q', mention is made of chlorine, bromine and iodine.

In this method, firstly, the compound represented by the general formula (II-3) is reacted with the equimolar amount of triphenylphosphine to produce the phosphonium salt derivative represented by the general formula (V). This reaction is conducted in a solvent, as exemplified by aromatic hydrocarbons such as benzene, toluene and xylene; ethers such as tetrahydrofuran, dioxane and dimethoxyethane; acetonitrile, and a mixture of these solvent. This reaction is conducted at temperature ranging from 10° C. to 200° C., preferably from 30° C. to 150° C., for 0.5 to 50 hours.

Then, the phosphonium salt (V) is subjected to condensation reaction with the aldehyde derivative (VI). The condensation of (V) with (VI) is conducted in an adequate solvent in the presence of a base. Examples of the solvent include alcohols such as methanol, ethanol and propanol; ethers such as ethyl ethers, dioxane, tetrahydrofuran and dimethoxyethane; aromatic hydrocarbons such as benzene, toluene and xylene; dichloromethane, 1,2-dichloroethane, N,N-dimethylformamide (DMF) and dimethyl sulfoxide (DMSO); and a mixture of these solvents. Examples of the base include alkali metal hydride such as sodium hydride and potassium hydride; alkoxides such as sodium ethoxide, sodium methoxide, potassium ethoxide and potassium tert-butoxide; organic lithium compounds such as methyl lithium and phenyl lithium; and sodium amide. The amount of these bases to be employed ranges preferably from about 1 to about 1.5 molar equivalents relative to the compound (V). This reaction is conducted at temperature usually ranging from −50° C. to 120° C., preferably from −20° C. to 80° C. The reaction time ranges from 0.5 to 50 hours. The compound (VII) is obtained as a mixture of (E)-isomer and (Z)-isomer. These isomers, as they are in the form of mixture or after isolating respectively, are subjected to reduction to produce (I-3). This reduction reaction is conducted, in accordance with a conventional method, in a solvent under hydrogen atmosphere in the presence of a catalyst as exemplified by a palladium catalyst (e.g., palladium-carbon and palladium black), a platinum catalyst (e.g., platinum oxide) and Raney nickel. Examples of the solvent include alcohols such as methanol, ethanol and propanol; ethers such as ethyl ether, dioxane, tetrahydrofuran and dimethoxyethane; aromatic hydrocarbons such as benzene, toluene and xylene; dichloromethane, 1,2-dichloroethane, ethyl acetate, acetonitrile, acetone, 2-butanone and N,N-dimethylformamide (DMF); and a mixture these solvent. The pressure of hydrogen atmosphere ranges from 1 to 150 atm., preferably from 1 to 20 atm.

The thienopyridine or thienopyrimidine derivative (I-3) thus obtained can be isolated and purified by a conventional means such as concentration, concentration under reduced pressure, solvent-extraction, crystallization, recrystallization, phasic transfer and chromatography.

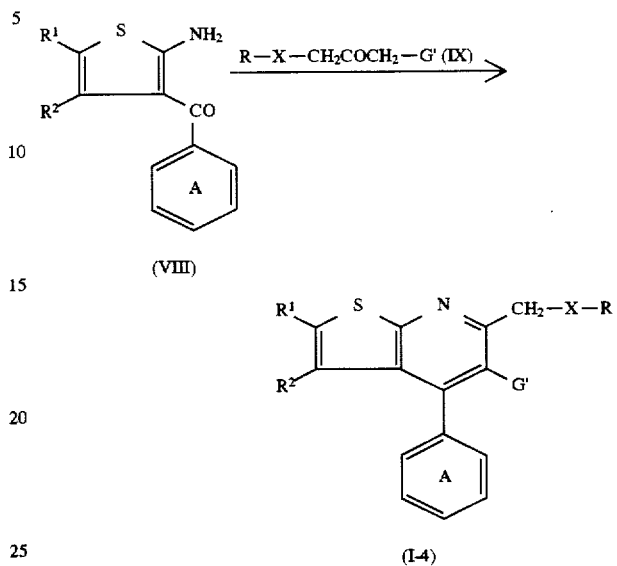

[wherein each symbol is of the same meaning as defined above].

In this method, the 2-amino-3-benzoylthiophene derivative (VIII) is allowed to react with (IX) in the presence of an acid to produce (I-4). The reaction of (VIII) with (IX) is conducted in an adequate solvent in the presence of an acid, for example, a Lewis acid such as aluminum chloride and zinc chloride; and hydrochloric acid, sulfuric acid, trifluoroacetic acid and p-toluenesulfonic acid. Examples of the solvent include aromatic hydrocarbons such as benzene, toluene and xylene; ethers such as tetrahydrofuran, dioxane and dimethoxyethane; alcohols such as methanol, ethanol and propanol; N,N-dimethylformamide (DMF), dimethyl sulfoxide (DMSO), chloroform, dichloromethane, 1,2-dichloroethane and 1,1,2,2-tetrachloroethane; and a mixture of these solvents. The amount of the compound (IX) to be employed ranges preferably from 1.0 to 2.0 molar equivalents relative to the compound (VIII). The amount of the acid to be employed ranges, preferably from 0.05 to 2.0 molar equivalents relative to the compound (VIII). This reaction is conducted at temperature usually ranging from 0° C. to 200° C., preferably from about 20° C. to 120° C. The reaction time ranges from 0.5 to 20 hours, preferably from 1 to 10 hours.

The thienopyridine derivative (I-4) thus obtained can be isolated and purified by a conventional separating and purifying means such as concentration, concentration under reduced pressure, solvent-extraction, crystallization, recrystallization, phasic transfer and chromatography.

Method E

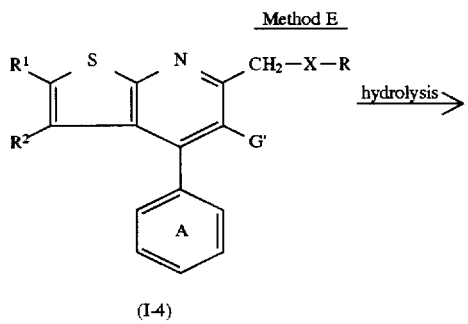
(I-4)

hydrolysis →

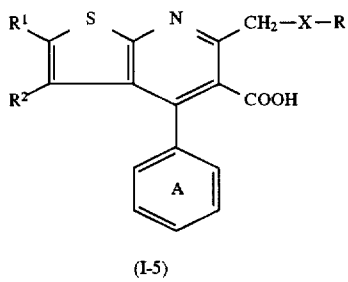
(I-5)

In this method, the ester derivative (I-4) is subjected to hydrolysis to produce the carboxylic acid derivative (I-5). The hydrolysis of the compound (I-4) is conducted, in accordance with a conventional method, in water or an aqueous solvent. Examples of the aqueous solvent include alcohols such as methanol, ethanol, 2-methoxyethanol, ethylene glycol, propanol and butanol; ethers such as tetrahydrofuran and dioxane; acetic acid, N,N-dimethylformamide, dimethyl sulfoxide, acetonitrile or acetone. This reaction is conducted in the presence of a base such as potassium carbonate, sodium carbonate, sodium hydroxide and potassium hydroxide, or an acid such as hydrochloric acid, sulfuric acid, acetic acid or hydrobromic acid. Preferably, the acid or the base is employed in an excess amount (base: 1.0 to 10 molar equivalent, acid: 2 to 50 molar equivalents) relative to the compound (I-4). The reaction temperature ranges usually from −20° C. to 150° C., preferably from −10° C. to 100° C., and the reaction time ranges from 1 to 50 hours.

The thienopyridine derivative (I-5) thus obtained can be isolated and purified by a conventional separating and purifying means such as concentration, concentration under reduced pressure, solvent-extraction, crystallization, recrystallization, phasic transfer and chromatography.

The starting compounds in Method A, Method B and Method C can be produced by, for example, the following method.

Method F

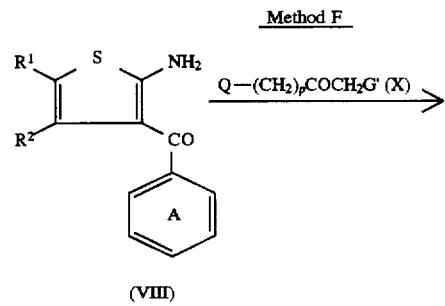
(VIII)

Q—(CH$_2$)$_p$COCH$_2$G' (X) →

-continued
Method F

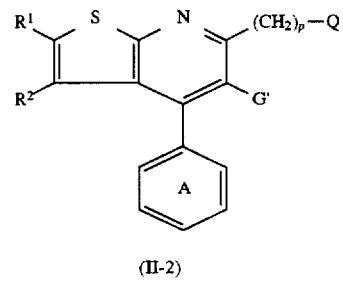
(II-2)

[wherein each symbol is of the same meaning as defined above].

In this method, 2-amino-3-benzoylthiophene derivative (VIII) is allowed to react with (X) in the presence of an acid to produce (II-2). This method is conducted in substantially the same manner as in Method D.

The thienopyridine derivative (II-2) thus obtained can be isolated and purified by a conventional separating and purifying means such as concentration, concentration under reduced pressure, solvent-extraction, crystallization, recrystallization, phasic transfer and chromatography.

The starting compound (VIII) in Method D and Method F can be produced in accordance with the methods described on Journal of Medicinal Chemistry, Vol.16, p.214 (1973), Journal of Medicinal Chemistry, Vol.17, p.624 (1974) and Japanese Patent Unexamined Publication No. 176591/1986. The compound (VIII) can be produced by, for example, substantially the same manner as shown in Reference Examples.

Method G (VIII) $\xrightarrow{\text{ClCH}_2\text{CN}}$

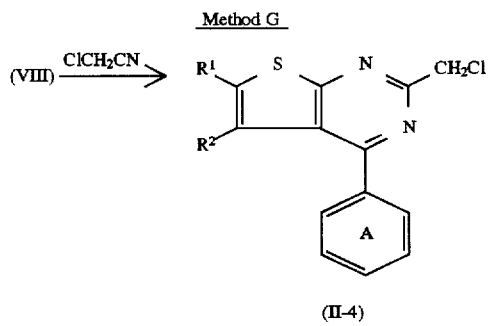
(II-4)

[wherein each symbol is of the same meaning as defined above].

In this method, the 2-amino-3-benzoylthiophene derivative (VIII) is allowed to react with chloroacetonitrile to produce the 2-chloromethyl compound (II-4). The reaction of (VIII) with chloroacetonitrile is conducted in the presence of an acid by using an excess volume of chloroacetonitrile as the solvent. As the acid, use is made of such ones as mentioned in Method D. The amount the acid to be employed ranges from about 1 to about 5 molar equivalents relative to the compound (VIII), preferably 1 to 3 molar equivalents. The reaction time ranges usually from 0.5 to 30 hours, preferably from 1 to 10 hours. The reaction temperature ranges usually from 20° C. to 200° C., preferably from 30° C. to 150° C.

The thienopyrimidine derivative (II-4) thus obtained can be isolated and purified by a conventional separating and purifying means such as concentration, concentration under reduced pressure, solvent-extraction, crystallization, recrystallization, phasic transfer and chromatography.

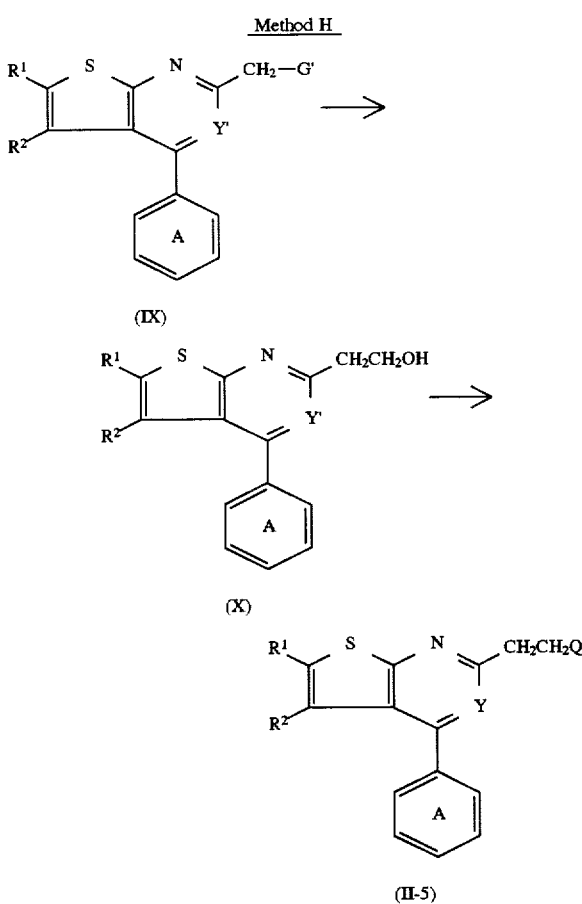

Method H (IX)

(X)

(II-5)

[wherein each symbol is of the same meaning as defined above].

In this method, the compound (IX) is subjected to reduction to produce the alcohol derivative (X), then, from the compound (X), the compound (II-5) is produced.

The reduction of the compound (IX) can be conducted by a per se known method, as exemplified by reduction with a metal hydride, reduction with a metal hydride complex, reduction with diborane or a substituted borane and catalytic hydrogenation. In other words, this reaction is conducted by treating the compound (IX) with a reducing agent. Examples of the reducing agent include alkali metal borohydride (e.g., sodium borohydride and lithium borohydride), a metal hydride complex such as lithium aluminum hydride, metal hydride such as sodium hydride, an organotin compound (e.g., triphenyltin hydride), a metal or metal salt such as a nickel compound and a zinc compound, a catalytic reduction agent using a transition-metal catalyst such as palladium, platinum or rhodium and hydrogen, and diborane. This reaction is conducted in an organic solvent inert to the reaction. Examples of the solvent include aromatic hydrocarbons such as benzene, toluene and xylene; halogenated hydrocarbons such as chloroform, carbon tetrachloride, dichloromethane, 1,2-dichloroethane and 1,1,2,2-tetrachloroethane; ethers such as diethyl ether, tetrahydrofuran and dioxane; alcohols such as methanol, ethanol, propanol, isopropanol and 2-methoxyethanol; amides such as N,N-dimethylformamide; or a mixture of these solvents, and, from among these solvents, a suitable one is selectively employed depending on kinds of the reducing agents. The reaction temperature ranges from −20° C. to 150° C., especially preferably from 0° C. to 100° C., and the reaction time ranges from about 1 to 24 hours.

Then, the compound (X) is allowed to react with a halogenating agent or a sulfonylating agent to produce (II-5). As the halogenating agent, use is preferably made of, for example, thionyl chloride and phosphorus tribromide, and, in this case, (II-5), in which Q is chlorine or bromine, is produced. This reaction is conducted in a suitable inert solvent (e.g., benzene, toluene, xylene, chloroform and dichloromethane) or in an excess volume of a halogenating agent, at temperature ranging from −10° C. to 80° C. The amount of the halogenating agent ranges from 1 to 20 mol. relative to (X). As the sulfonylating agent, use is preferably made of, for example, mesyl chloride, tosyl chloride and benzenesulfonyl chloride to yield (II-5) in which Q is mesyloxy, tosyloxy or benzenesulfonyloxy. This reaction is conducted in a suitable inert solvent (e.g., benzene, toluene, xylene, ethyl ether, ethyl acetate, tetrahydrofuran, chloroform and dichloromethane) in the presence of a base (e.g., triethylamine, N-methylmorpholine, sodium hydrogencarbonate, potassium hydrogencarbonate, sodium carbonate and potassium carbonate) at temperature ranging from −10° C. to 50° C. The amounts of the sulfonylating agent and the base are respectively in the range from 1 to 1.5 molar equivalents relative to one mol. of (X). By allowing 1 to 1.5 mol. of sodium iodide or potassium iodide to react with the compound (II-5) thus produced, in which Q is chlorine, bromine or sulfonyloxy, the compound (II-5) in which Q is iodine can also be produced. In this case, the reaction can be conducted in a solvent such as acetone, methyl ethyl ketone, methanol or ethanol at temperature ranging from 20° to 80° C.

The thienopyridine or thienopyrimidine derivative (II-5) thus obtained can be isolated and purified by a conventional separating and purifying means such as concentration, concentration under reduced pressure, solvent-extraction, crystallization, recrystallization, phasic transfer and chromatography.

The compound (IX) to be employed in Method H can be produced in accordance with, for example Method I or Method J.

Method I

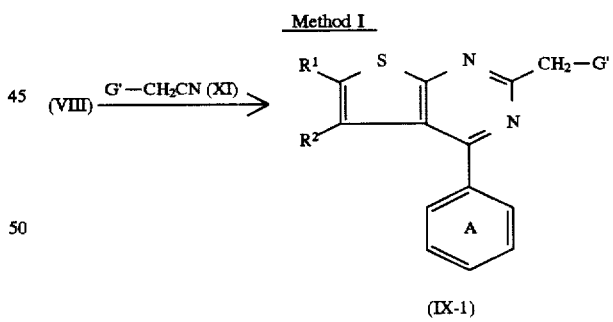

(IX-1)

[wherein each symbol is of the same meaning as defined above].

In this method, the 2-amino-3-benzoylthiophene derivative (VIII) is allowed to react with the cyanoacetic ester derivative (XI) to produce the thienopyrimidine derivative (IX-1). The reaction of (VIII) with (XI) is conducted in substantially the same manner as in Method G.

The thienopyrimidine derivative (IX-1) thus obtained can be isolated and purified by a conventional separating and purifying means such as concentration, concentration under reduced pressure, solvent-extraction, crystallization, recrystallization, phasic transfer and chromatography.

Method J

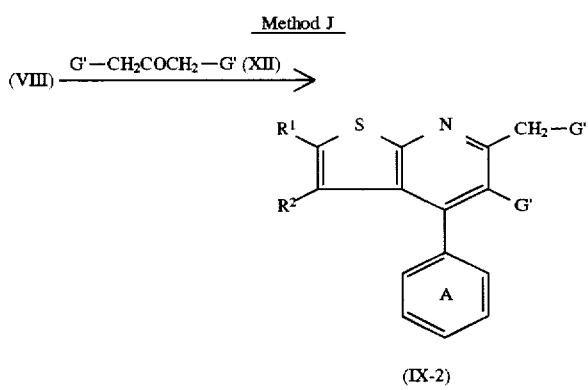

[wherein each symbol is of the same meaning as defined above].

In this method, the 2-amino-3-benzoylthiophene derivative (VIII) is allowed to react with the acetonedicarboxylic acid ester derivative (XII) to produce the thienopyridine derivative (IX-2). The reaction of (VIII) with (XII) is conducted substantially the same manner as in Method D.

The thienopyridine derivative (IX-2) thus obtained can be isolated and purified by a conventional means such as concentration, concentration under reduced pressure, solvent-extraction, crystallization, phasic transfer and chromatography.

Excellent anti-arthritis activities of the compound (I) and its salts provided by the present invention were confirmed in an experimental model of adjuvant arthritis causing arthritis similar to human rheumatoid arthritis. The objective compounds may inhibit the production of cytokines such as interleukin-2 and interferon-γ. And, the toxicity of the compounds of this invention is low. Therefore, the object compounds of this invention can be applied to all types of arthritis presenting inflammatory symptoms at synovial joints of mammalian animals including man (e.g., humans, cattle, horses, swine, dogs, cats, and the like).

And, excellent bone resorption inhibiting activities of the compound (I) and its salts provided by the present invention were confirmed in the experiment as mentioned below. Therefore, the object compounds of this invention can be used as a bone resorption inhibiting agent or an agent for the prophylaxis or treatment of osteoporosis by administering to the above-mentioned mammalian animals including man.

While the dosage of the compound (I) employed in this invention can be selected depending on the administration routes and symptoms of the patients to be treated, it ranges, in oral administration, from 5 mg to 1000 mg per adult person, and, in non-oral administration, from 1 mg to 100 mg once to divided into three times a day.

The test method and its results supporting the pharmacological activities of the compound (I) of this invention or its salts are shown below.

TEST EXAMPLE 1
Action against rat adjuvant arthritis

Male Lewis rats (7 weeks of age, Japan Clea) were sensitized by intracutaneous injection of 0.05 ml of Freund's complete adjuvant (0.5% dead tubercle bacillus cell suspension in liquid paraffin) at the right hind paw. The test drug (25 mg/kg or 12.5 mg/kg), in suspension in 0.5% methyl cellulose, was once daily for 14 days starting just before the sensitization (day 0). On days 0 and 14, the animal's left hind paw volume and body weight were measured by a plethysmometer (Ugo Basile, Italy) and a electric balance (EB-3200D, Shimazu, Japan), respectively, and percent paw swelling suppression and percent body weight gain, relative to non-sensitized control rats, were determined.

The results, expressed in mean ±S.E. for 6 animals in each group, were compared and statistically analyzed by Dunnett's test. Level of significance was set below 5%. As shown in Table 1, the compound of the present invention effectively suppressed paw edema and improved systemic conditions as demonstrated by body weight gain.

TABLE 1

| Compound (Ex. No.) | Dose (mg/kg) | Percent Swelling Suppression (%) | Body Weight Gain[1] Rate (%) |
| --- | --- | --- | --- |
| 1 | 25.0 | 66** | 16** |
| 27 | 12.5 | 54** | 15* |
| 28 | 12.5 | 72** | 23** |

1) $\dfrac{\text{(drug-treated rats)} - \text{(sensitized control rats)}}{\text{(normal control rats)} - \text{(sensitized control rats)}} \times 100\,(\%)$

*p < 0.05
**p < 0.01 (relative to control)

TEST EXAMPLE 2
Bone resorption suppressing action

Bone resorption was measured by the method of Raisz [Journal of Clinical Investigation, 44, 103–116(1965)]. Specifically, one Sprague-Dawley rat, at 18 days of gestation, was given 50 µCi of $^{45}$Ca (calcium isotope, in $CaCl_2$ solution) by subcutaneous injection. On the following day, the animal was laparotomized and fetal rats aseptically removed. Both forearm bones (radius and ulna) were cut out from the body of each fetus under an anatomical microscope, and connective tissue and cartilages were removed to the maximum possible extent, to prepare bone culture samples. Each bone fragment was pre-cultured at 37° C. for 24 hours in 0.6 ml of BGJb medium (Fitton-Jackson modification, GIBCO Laboratories, United States) prepared by adding bovine serum albumin (final concentration 2 mg/ml), after which it was transferred to the same medium as above but containing a compound (final concentration 30 µM) and cultured for two more days. $^{45}$Ca radioactivity in the medium and $^{45}$Ca radioactivity in the bone were then measured, and the percent ratio of $^{45}$Ca released from the bone to the medium was calculated using the following equation:

Percent ratio of $^{45}$Ca released from bone to medium =

$$\dfrac{[(^{45}\text{Ca count in the medium})]}{[(^{45}\text{Ca count in the medium}) + (^{45}\text{Ca count in the bone})]} \times 100$$

For control, bone fractions from fetuses of the same litter were cultured for two days in the absence of the test compound. The mean q standard deviation for the values from five bone fragments in a group was calculated, and percent ratio to the control was calculated. The result of compound obtained in Example 27 (bone resorption inhibitory activity) was 76.5%.

EXAMPLES

By way of the following Reference Examples and Examples, the present invention will be described in more specifically, but they are not intended to limit the scope of the invention thereto.

Reference Example 1

A solution of ethyl 3,4-dimethoxybenzoate (17.8 g) and acetonitrile (7.0 g) in toluene (30 ml) was added dropwise at 100° C. to a suspension of sodium hydride (60% in oil, 6.8 g) in toluene (170 ml) and N,N-dimethylformamide (DMF) (17 ml). The mixture was stirred for three hours at 100° C. The reaction mixture was poured into ice-water. The organic layer was separated. The aqueous layer was acidified with 2N HCl, which was subjected to extraction with ethyl acetate. The ethyl acetate layer was washed with water and dried (MgSO₄), followed by distilling off the solvent under reduced pressure to leave ω-cyano-3,4-dimethoxyacetophenone (14.0 g, 80%). Recrystallization from ethyl acetate gave colorless needles, m.p.141°–142° C.

Reference Example 2

In substantially the same manner as in Reference Example 1, ω-cyano-3,4-methylenedioxyacetophenone was produced. Recrystallization from ethyl acetate-hexane gave colorless prisms, m.p.135°–136° C.

Reference Example 3

A mixture of ω-cyano-3,4-dimethoxyacetophenone (7.0 g), sulfur (1.2 g), 2-butanone (2.46 g), morpholine (3.5 ml) and ethanol (20 ml) was stirred for two hours under reflux. The reaction mixture was poured into ice-water, which was washed with 2N HCl, 1N KOH and water, successively, then dried (MgSO₄), followed by distilling off the solvent under reduced pressure to leave 2-amino-3-(3,4-dimethoxybenzoyl)-4,5-dimethylthiophene (4.1 g, 41%). Recrystallization from ethyl acetate-hexane gave yellow prisms, m.p.172°–173° C.

Reference Examples 4 and 5

In substantially the same manner as in Reference Example 3, compounds shown in Table 2 were produced.

Reference Example 6

A mixture of 2-amino-3-(3,4-dimethoxybenzoyl)-4,5-dimethylthiophene (3.6 g), ethyl 4-chloroacetoacetate (2.1 g), concentrated sulfuric acid (0.5 ml) and acetic acid (50 ml) was stirred for two hours at temperature ranging from 90° to 100° C. The reaction mixture was concentrated under reduced pressure. The concentrate was poured into water, which was neutralized with potassium carbonate, followed by extraction with chloroform. The chloroform layer was washed with water and dried (MgSO₄), then the solvent was distilled off under reduced pressure. The residue was subjected to column chromatography on silica gel. From the fractions eluted with chloroform-hexane (4:1, v/v), ethyl 6-chloromethyl-4-(3,4-dimethoxyphenyl)-2,3-dimethylthieno[2,3-b]pyridine-5-carboxylate (3.5 g, 67%) was obtained. Recrystallization from ethyl acetate-hexane gave colorless prisms, m.p.162°–163° C.

Reference Examples 7 and 8

In substantially the same manner as in Reference Example 6, compounds shown in Table 3 were produced.

TABLE 2

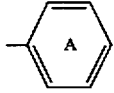

| R. Ex. No. | R¹ | R² | A | m.p. (°C.) | Recrystallization solvent |
|---|---|---|---|---|---|
| 4 | CH₃ | CH₃ | 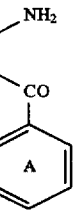 | 124–125 | ethyl acetate-hexane |
| 5 | —(CH₂)₄— | |  | 154–155 | ethyl acetate-hexane |

TABLE 3

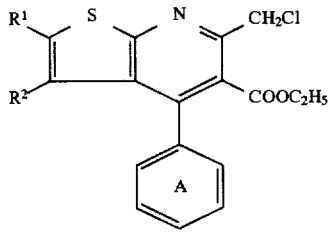

| R. Ex. No. | $R^1$ | $R^2$ | A | m.p. (°C.) | Recrystallization solvent |
|---|---|---|---|---|---|
| 7 | $CH_3$ | $CH_3$ | 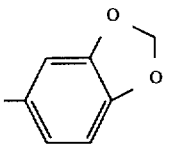 | 148–149 | ethyl acetate-hexane |
| 8 | $-(CH_2)_4-$ | | 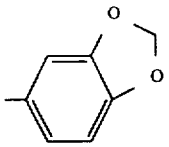 | 142–143 | ethyl acetate-hexane |

Reference Example 9

In substantially the same manner as in Reference Example 3, 2-amino-3-(4-chlorobenzoyl)-4,5-dimethylthiophene was produced. Recrystallization from ethyl acetate-hexane gave yellow plates. m.p.122°– 123° C.

Reference Example 10

In substantially the same manner as in Reference Example 3, 2-amino-3-(4-chlorobenzoyl)-4-methyl-5-propylthiophene was produced. Recrystallization from ethanol gave yellow prisms. m.p.94°–95° C.

Reference Example 11

In substantially the same manner as in Reference Example 3, 2-amino-3-(4-methoxybenzoyl)4,5-dimethylthiophene was produced. Recrystallization from ethyl acetate-hexane gave yellow prisms. m.p.132°–133° C.

Reference Example 12

In substantially the same manner as in Reference Example 6, ethyl 6-chloromethyl-4-(4-chlorophenyl)-2,3-dimethylthieno[2,3-b]pyridine-5-carboxylate was produced. Recrystallization from ethyl acetate-hexane gave colorless prisms, m.p.132°–144° C.

Reference Example 13

In substantially the same manner as in Reference Example 6, ethyl 6-chloromethyl-4-(4-chlorophenyl)-3-methyl-2-propylthieno[2,3-b)pyridine-5-carboxylate was produced. Recrystallization from ethyl acetate-hexane gave colorless prisms, m.p.95°–96° C.

Reference Example 14

In substantially the same manner as in Reference Example 6, ethyl 6-chloromethyl-4-(4-methoxyphenyl)-2,3-dimethylthieno[2,3-b]pyridine-5-carboxylate. Recrystallization from ethyl acetate-hexane gave colorless prisms, m.p.110°–111° C.

Reference Example 15

To a mixture of 2-amino-3-(3,4-dimethoxybenzoyl)-4,5-dimethylthiophene (3.0 g) and chloroacetonitrile (11 g) was added, in limited amounts, powdered aluminum chloride (2.75 g). The mixture was stirred for 2.5 hours at 100° C. The reaction mixture was poured into ice-water, which was subjected to extraction with chloroform. The chloroform layer was washed with a saturated aqueous solution of sodium hydrogencarbonate and water, which was dried ($MgSO_4$). Chloroform was distilled off, and the residue was subjected to column chromatography on silica gel. From the fraction eluted with dichloromethane, 2-chloromethyl-4-(3, 4-dimethoxyphenyl)-5,6-dimethylthieno[2,3-d]pyrimidine (1.58 g, 44%) was obtained. Recrystallization from ethyl acetate-hexane gave colorless prisms, m.p.117°–118° C.

Reference Examples 16 to 31

In substantially the same manner as in Reference Example 3, compounds shown in Table 4 were produced.

TABLE 4

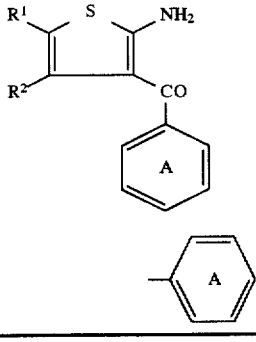

| Ref. Ex. No. | R¹ | R² | A | m.p. (°C.) | Recrystallization solvent |
|---|---|---|---|---|---|
| 16 | | —CH₂S(CH₂)₂— | 2,3-(OCH₃)₂-phenyl | 197–198 | ethyl acetate-hexane |
| 17 | | —CH₂S(CH₂)₂— | 3,5-(OCH₃)₂-phenyl | 156–157 | ethanol |
| 18 | | —CH₂O(CH₂)₂— | 2,3-(OCH₃)₂-phenyl | 118–119 | ethyl acetate-hexane |
| 19 | | —CH₂O(CH₂)₂— | 3,5-(OCH₃)₂-phenyl | 152–153 | ethanol |
| 20 | CH₃ | CH₃ | 2,3,4-(OCH₃)₃-phenyl | 135–136 | ethyl acetate-hexane |
| 21 | CH₃ | CH₃ | 2,4-(OCH₃)₂-phenyl | 181–182 | ethyl acetate-hexane |
| 22 | CH₃ | CH₃ | 3,5-(OCH₃)₂-phenyl | 154–155 | ethyl acetate-hexane |
| 23 | | —CH₂—N(CH₃)—(CH₂)₂— | 3,4-(OCH₃)₂-phenyl | 180–182 | ethanol |

TABLE 4-continued
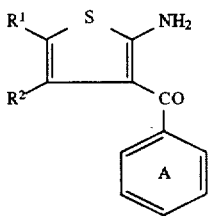
| Ref. Ex. No. | R¹ | R² | A | m.p. (°C.) | Recrystallization solvent |
|---|---|---|---|---|---|
| 24 | | —CH₂—N(CH₂C₆H₅)—(CH₂)₂— | 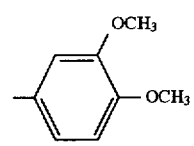 | 149–150 | ethanol |
| 25 | CH₃ | CH₃ | 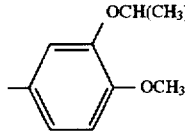 | 162–163 | ethanol |
| 26 | | —CH₂—N(CH₂C₆H₅)—(CH₂)₂— | 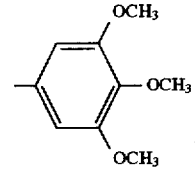 | 119–120 | ethyl acetate-hexane |
| 27 | | —CH₂—N(CH₂C₆H₅)—(CH₂)₂— | 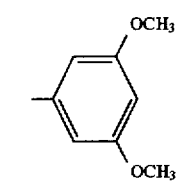 | 157–159 | ethyl acetate-hexane |
| 28 | | —CH₂—N(C₂H₅)—(CH₂)₂— | 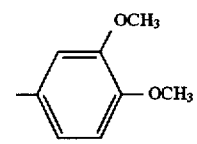 | 190–192 | ethanol |
| 29 | | —CH₂—N(C₃H₇)—(CH₂)₂— | 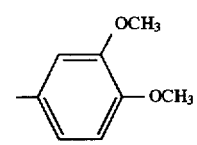 | 161–162 | ethanol |
| 30 | | —CH₂—N—(CH₂)₂—<br>         \|<br>       CH₂—C₆H₄—OCH₃ | 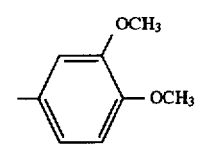 | 165–166 | ethanol |
| 31 | | —CH₂—N(CH₂C₆H₅)—(CH₂)₂— | 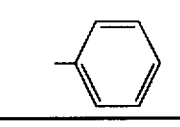 | 187–188 | ethanol |

Reference Example 32

A solution of acetonitrile (33.6 g) was added dropwise at −70° C. to a mixture of n-butyllithium in hexane (1.6M, 511 ml) and tetrahydrofuran (900 ml). After the mixture was stirred for 45 minutes at −70° C., a solution of ethyl 2,4-dimethoxybenzoate (86.0 g) in tetrahydrofuran (100 ml) was added dropwise at the same temperature (−70° C.). The reaction mixture was stirred for 30 minutes at −70° C., and acidified with 2N HCl. After stirring for 30 minutes at room temperature, the crystals were separated by filtration to leave ω-cyano-2,4-dimethoxyacetophenone (52.3 g, 62%). Recrystallization from ethyl acetate-hexane gave colorless prisms, m.p. 154°–155° C.

Reference Example 33

In substantially the same manner as in Reference Example 32, ω-cyano-3,5-dimethoxyacetophenone (52.3 g, 62%) was produced. Recrystalization from ethyl acetate-hexane gave colorless prisms, m.p. 118°–119° C.

Reference Example 34

In substantially the same manner as in Reference Example 32, ω-cyano-3-isopropoxy-4-methoxyacetophenone (52.3 g, 62%) was produced. Recrystalization from ethyl acetate-hexane gave colorless prism, m.p. 102°–104° C.

Reference Examples 35 to 49

In substantially the same manner as in Reference Example 6, compounds shown in Table 5 were produced.

TABLE 5

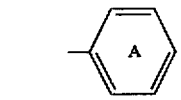

| Ref. Ex. No. | $R^1$ | $R^2$ | —⟨A⟩ | m.p. (°C.) | Recrystallization solvent |
|---|---|---|---|---|---|
| 35 |  | —CH$_2$S(CH$_2$)$_2$— | 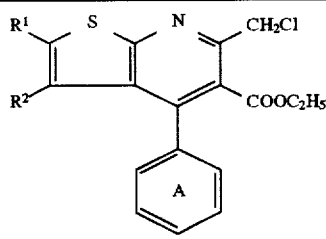 2-OCH$_3$, 3-OCH$_3$ | 187–188 | ethyl acetate-hexane |
| 36 |  | —CH$_2$S(CH$_2$)$_2$— | 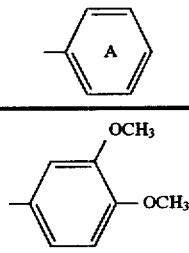 3-OCH$_3$, 5-OCH$_3$ | 145–146 | ethyl acetate-hexane |
| 37 |  | —CH$_2$O(CH$_2$)$_2$— | 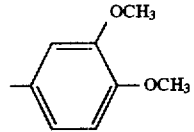 2-OCH$_3$, 3-OCH$_3$ | 142–143 | ethanol |
| 38 | CH$_3$ | CH$_3$ | 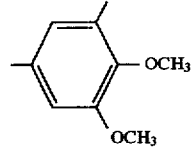 2-OCH$_3$, 3-OCH$_3$, 4-OCH$_3$ | 119–120 | ethyl acetate-hexane |
| 39 | CH$_3$ | CH$_3$ | 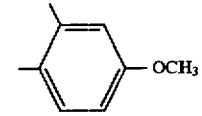 3-OCH$_3$, 4-OCH$_3$ | 108–109 | ethanol |

TABLE 5-continued
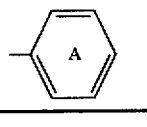
| Ref. Ex. No. | R¹ | R² | A | m.p. (°C.) | Recrystallization solvent |
|---|---|---|---|---|---|
| 40 | $CH_3$ | $CH_3$ | 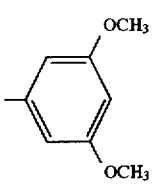 | 143–145 | ethanol |
| 41 | $-CH_2-N(CH_3)-(CH_2)_2-$ | | 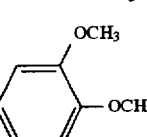 | 98–100 | ethanol |
| 42 | $-CH_2-N(CH_2C_6H_5)-(CH_2)_2-$ | | 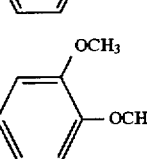 | 120–121 | ethyl acetate-hexane |
| 43 | $CH_3$ | $CH_3$ | 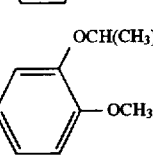 | 168–169 | ethanol |
| 44 | $-CH_2-N(CH_2C_6H_5)-(CH_2)_2-$ | | 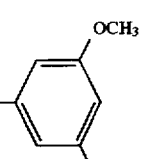 | 135–136 | ethyl acetate-hexane |
| 45 | $-CH_2-N(CH_2C_6H_5)-(CH_2)_2-$ | | 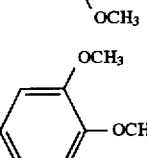 | 124–125 | ethyl acetate-hexane |
| 46 | $-CH_2-N(C_2H_5)-(CH_2)_2-$ | | 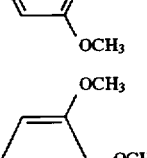 | 132–133 | ethyl acetate-hexane |
| 47 | $-CH_2-N(C_3H_7)-(CH_2)_2-$ | | 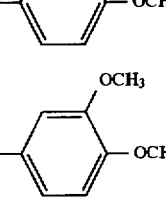 | 136–138 | ethyl acetate-ether |

TABLE 5-continued

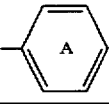

| Ref. Ex. No. | R¹ | R² | A (ring) | m.p. (°C.) | Recrystallization solvent |
|---|---|---|---|---|---|
| 48 | —CH₂—N—(CH₂)₂— with CH₂–C₆H₄–OCH₃ branch | | 3,4-(OCH₃)₂-C₆H₃ | 129–130 | ethyl acetate-hexane |
| 49 | —CH₂—N(CH₂C₆H₅)—(CH₂)₂— | | C₆H₅ | 141–142 | ethyl acetate-hexane |

Example 1

A mixture of ethyl 6-chloromethyl-4-(3,4-dimethoxyphenyl)-2,3-dimethylthieno[2,3-b]pyridine-5-carboxylate (1.5 g), diethylamine (1.04 g) and dichloromethane (35 ml) was stirred for 14 hours under reflux. The reaction mixture was washed with water and dried (MgSO₄), then the solvent was distilled off. The residue was subjected to column chromatography on silica gel. From the fraction eluted with chloroform, ethyl 6-(N,N-diethylaminomethyl)-4-(3,4-dimethoxyphenyl)-2,3-dimethylthieno[2,3-b]pyridine-5-carboxylate (1.1 g, 68%) was obtained. Recrystallization from ethyl acetate-hexane gave colorless prisms, m.p.110°–111° C.

Example 2

Sodium hydride (60% in oil, 0.171 g) was added to a solution of 1H-1,2,4-triazole (0.271 g) in N,N-dimethylformamide (DMF) (15 ml). The mixture was stirred for 15 minutes at room temperature, to which was added ethyl 6-chloromethyl-4-(3,4-dimethoxyphenyl)-2,3-dimethylthieno[2,3-b]pyridine-5-carboxylate (1.5 g). The mixture was stirred for 35 minutes at 80° C. The reaction mixture was poured into water, which was subjected to extraction with ethyl acetate. The ethyl acetate layer was washed with water and dried (MgSO₄), then the solvent was distilled off. The residue was subjected to column chromatography on silica gel. From the fraction eluted with chloroform-methanol (30:1, v/v), ethyl 4-(3,4-dimethoxyphenyl)-2,3-dimethyl-6-(1,2,4-triazol-1-ylmethyl)thieno[2,3-b]pyridine-5-carboxylate (1.0 g, 62%) was obtained. Recrystallization from ethyl acetate-hexane gave colorless prisms, m.p.136°–137° C.

Example 3

In the column chromatography of Example 2, from the fraction eluted succeeding to ethyl 4-(3,4-dimethoxyphenyl)-2,3-dimethyl-6-(1,2,4-triazol-1-ylmethyl)thieno[2,3-b]pyridine-5-carboxylate, was obtained ethyl 4-(3,4-dimethoxyphenyl)-2,3-dimethyl-6-(1,2,4-triazol-4-ylmethyl)thieno[2,3-b]pyridine-5-carboxylate (0.12 g, 8%). Recrystallization from ethyl acetate-hexane gave colorless prisms, m.p.187°–188° C.

Example 4

In substantially the same manner as in Example 2, ethyl 6-chloromethyl-4-(3,4-methylenedioxyphenyl)-2,3-dimethylthieno[2,3-b]pyridine-5-carboxylate was allowed to react with 1H-1,2,4-triazole to produce ethyl 2,3-dimethyl-4-(3,4-methylenedioxyphenyl)-6-(1,2,4-triazol-1-ylmethyl)thieno[2,3-b]pyridine-5-carboxylate. Recrystallization from ethyl acetate-hexane gave colorless prisms, m.p.109°–110° C.

Example 5

In the column chromatography of Example 4, from the fraction eluted succeeding to ethyl 2,3-dimethyl-4-(3,4-methylenedioxyphenyl)-6-(1,2,4-triazol-1-ylmethyl)thieno[2,3-b]pyridine-5-carboxylate, was obtained ethyl 2,3-dimethyl-4-(3,4-methylenedioxyphenyl)-6-(1,2,4-triazol-4-ylmethyl)thieno[2,3-b]pyridine-5-carboxylate. Recrystallization from ethyl acetate-hexane gave colorless prisms, m.p.96°–98° C.

Example 6

A mixture of ethyl 6-chloromethyl-4-(3,4-methylenedioxyphenyl)-2,3-dimethylthieno[2,3-b]pyridine-5-carboxylate (1.5 g), diethylamine (1.36 g) and dichloromethane (35 ml) was stirred for 14 hours under reflux. The reaction mixture was washed with water and dried (MgSO₄), then the solvent was distilled off. The residue was subjected to column chromatography on silica gel. From the fraction eluted with chloroform, was obtained ethyl 6-(N,N-diethylaminomethyl)-4-(3,4-methylenedioxyphenyl)-2,3-dimethylthieno[2,3-b]pyridine-5-carboxylate as an oily product. This oily product was dissolved in ethanol (35 ml), to which was added ethanolic hydrogen chloride (23%, 1.2 g). The mixture was stirred for 15 minutes at room temperature, which was concentrated under reduced pressure to leave hydrochloride of ethyl 6-(N,N-diethylaminomethyl)-4-(3,4-methylenedioxyphenyl)-2,3-dimethylthieno[2,3-b]pyridine-5-carboxylate (0.8 g, 44%) as an amorphous solid product.

NMR(δppm, in CDCl$_3$): 1.03(3H,t,J=7 Hz), 1.54(6H,broad s), 1.71(3H,s), 2.48(3H,s), 3.15–3.80(4H, broad), 4.12 (2H,q,J=7 Hz), 4.50(2H,s), 6.04(1H,d,J=1.4 Hz), 6.06 (1H,d,J=1.4 Hz), 6.65–6.80(1H,d,J=7.6 Hz).

Elemental Analysis for $C_{24}H_{29}ClN_2O_4S \cdot 1/2H_2O$:

Calcd.: C,59.30; H,6.22; N,5.76

Found: C,59.28; H,6.54; N,5.68

Examples 7 to 9

In substantially the same manner as in Example 2, the compound of Example 7 (Table 6) was obtained. In the column chromatography of Example 7, from the fraction eluted succeedingly, the compound of Example 8 (Table 6) was obtained. In substantially the same manner as in Working Example 6, the compound of Example 9 (Table 6) was produced.

2.75–2.93(2H,m), 3.84(1H,d,J=13.6 Hz), 3.96(2H,q,J=7.4 Hz), 3.98(1H,d,J=13.6 Hz), 6.00(1H,d,J=1.4 Hz), 6.04 (1H,d,J=1.4 Hz), 6.71(1H,dd,J=8.2&1.6 Hz), 6.78(1H,d, J=1.6 Hz), 6.82(1H,d,J=8.2 Hz).

Example 10

A mixture of ethyl 6-chloromethyl-4-(3,4-dimethoxyphenyl)-2,3-dimethylthieno(2,3-b|pyridine-5-carboxylate (0.75 g), 1-methyl-2-mercaptoimidazole (0.23 g), potassium carbonate (0.28 g) and N,N-dimethylformamide (10 ml) was stirred for one hour at 60° C. The reaction mixture was poured into water, which was subjected to extraction with ethyl acetate. The ethyl acetate layer was washed with water and dried (MgSO$_4$), then the solvent was distilled off to leave ethyl 4-(3,4-dimethoxyphenyl)-2,3-dimethyl-6-(1-methylimidazol-2-thiomethyl)thieno[2,3-b]pyridine-5-carboxylate (0.39 g, 43%). Recrystallization from ethyl acetate-hexane gave colorless needles, m.p.121°–122° C.

Example 11

A mixture of 2-chloromethyl-4-(3,4-dimethoxyphenyl)-5,6-dimethylthieno[2,3-d]pyrimidine (1.0 g), diethylamine

TABLE 6

| W. Ex. No. | R$^1$ | R$^2$ | A | R | m.p. (°C.) | Recrystallization solvent |
|---|---|---|---|---|---|---|
| 7 | —(CH$_2$)$_4$— | |  | 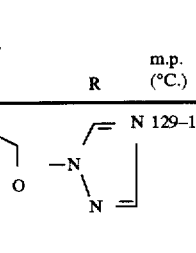 | 129–130 | ethyl acetate-hexane |
| 8 | —(CH$_2$)$_4$— | |  | 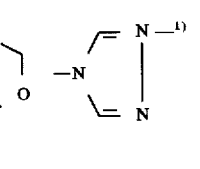$^{1)}$ | | |
| 9 | —(CH$_2$)$_4$— | |  | —N(C$_2$H$_5$)$_2$ $^{2)}$ | | |

1) NMR(δppm, in CDCl$_3$): 0.95(3H,t,J=7.2 Hz), 1.51–2.07 (6H,m), 2.80–2.90(2H,m), 4.02(2H,q,J=7.2 Hz), 5.39(2H, s), 6.03(1H,d,J=1.2 Hz), 6.07(1H,d,J=1.2 Hz), 6.68(1H, dd,J=8&2 Hz), 6.73(1H,d,J=2 Hz), 6.84(1H,d,J=8 Hz), 8.34(2H,s).

2) NMR(δppm, in CDCl$_3$): 0.94(3H,t,J=7 Hz), 0.99(3H,t,J= 7.4 Hz), 1.50–2.07(6H,m), 2.52(4H,q,J=7.4 Hz), (1.2 ml) and dichloromethane (30 ml) was stirred for 16 hours under reflux. The reaction mixture was concentrated under reduced pressure, which was dissolved in ethyl acetate. The ethyl acetate layer was washed with water and dried (MgSO$_4$), then the solvent was distilled off. The residue was subjected to column chromatography on silica gel. From the fraction eluted with ethyl acetate-methanol (5:1, v/v), was obtained 4-(3,4-dimethoxyphenyl)-5,6-dimethyl-2-(N,N-dimethylamino-methyl)thieno[2,3-d]pyrimidine (0.49 g, 44%). Recrystallization from isopropyl ether gave colorless prisms, m.p.118°–120° C.

Example 12

In substantially the same manner as in Example 6, ethyl 4-(4-chlorophenyl)-6-(N,N-diethylaminomethyl)-2,3-dimethylthieno[2,3-b]pyridine-5-carboxylate was produced. Recrystallization from ethyl acetate-hexane gave colorless prisms, m.p.98°–100° C.

Example 13

In substantially the same manner as in Example 6, ethyl 4-(4-chlorophenyl)-6-(N,N-diethylaminomethyl)-3-methyl-2-propylthieno[2,3-b]pyridine-5-carboxylate was produced. Recrystallization from ethyl acetate-hexane gave colorless prisms, m.p.82°–83° C.

Example 14

In substantially the same manner as in Example 6, ethyl 6-(N,N-diethylaminomethyl)-4-(4-methoxyphenyl)-2,3-dimethylthieno[2,3-b]pyridine-5-carboxylate was produced. Recrystallization from ethyl acetate-hexane gave colorless prisms, m.p.116°–118° C.

Example 15

Sodium hydride (60% in oil, 0.158 g) was added to a solution of 1H-1,2,4-triazole (0.252 g) in N,N-dimethylformamide (DMF) (15 ml). The mixture was stirred for 15 minutes at room temperature, to which was added ethyl 6-chloromethyl-4-(4-chlorophenyl)-2,3-dimethylthieno[2,3-b]pyridine-5-carboxylate (1.2 g). The mixture was stirred for 35 minutes at 80° C. The reaction mixture was poured into water, which was subjected to extraction with ethyl acetate. The ethyl acetate layer was washed with water and dried (MgSO$_4$), then the solvent was distilled off. The residue was subjected to column chromatography on silica gel. From the fraction eluted with dichloromethane-ethyl acetate (20:1, v/v), was obtained ethyl 4-(4-chlorophenyl)-2,3-dimethyl-6-(1,2,4-triazol-1-ylmethyl)thieno[2,3-b]pyridine-5-carboxylate (0.655 g, 50%). Recrystallization from ethanol gave colorless prisms, m.p.144°–145° C.

Example 16

In the column chromatography of Example 15, from the fraction eluted succeeding to ethyl 4-(4-chlorophenyl)-2,3-dimethyl-6-(1,2,4-triazol-1-ylmethyl)thieno[2,3-b]pyridine-5-carboxylate, was obtained ethyl 4-(4-chlorophenyl)-2,3-dimethyl-6-(1,2,4-triazol-4-ylmethyl)thieno[2,3-b]pyridine-5-carboxylate (0.085 g, 7%). Recrystallization from ethyl acetate-hexane gave colorless prisms, m.p.138°–139° C.

Examples 17 to 30 and Examples 35 to 41

In substantially the same manner as in Example 1, compounds of Examples 17 to 19, 22 to 28 and 35 to 41 were produced. In substantially the same manner as in Example 2, a compound of Example 20 was produced. The compound of Example 21 was obtained from the fraction eluted succeeding to the compound of Example 20 in the column chromatography of Example 20. In substantially the same manner as in Example 2, a compound of Example 29 was produced. A compound of Example 30 was obtained from the fraction eluted succeeding to the compound of Example 29 in the column chromatography of Example 29.

Example 31

A mixture of the compound (1.2 g) obtained in Reference Example 42, 1H-1,2,4-triazole (0.170 g), potasium carbonate (0.308 g) and acetone (30 ml) was stirred for 9 hours under reflux. The reaction mixture was poured into water, which was subjected to extraction with ethyl acetate. The ethyl acetate layer was washed with water and dried (MgSO$_4$), then the solvent was distilled off. The residue was subjected to column chromatography on silica gel. From the fraction eluted with ethyl acetate, was obtained a compound of Example 31.

Example 32

A compound of Example 32 was obtained from the fraction eluted succeeding to the compound of Example 31 in the column chromatography of Example 31.

Example 33

A mixture of the compound (1.2 g) obtained in Reference Example 44, imidazole (0.183 g), potassium carbonate (0.308 g) and acetone (30 ml) was stirred for 30 hours under reflux. The reaction mixture was poured into water, which was subjected to extraction with ethyl acetate. The ethyl acetate layer was washed with water and dried (MgSO$_4$), followed by distilling off the solvent to leave a compond of Example 33.

Example 34

A mixture of the compound (1.0 g) obtained in Reference Example 44, 2-mercapto-1-methylimidazole (0.24 g), potasium carbonate (0.257 g) and N,N-dimethylformamide (10 ml) was stirred for 4 hours at room temperature. The reaction mixture was poured into water, which was subjected to extraction with ethyl acetate. The ethyl acetate layer was washed with water and dried (MgSO$_4$), followed by distilling off the solvent to leave a compound of Example 34.

Compounds of Examples 17 to 41, which were produced as mentioned above, were shown in Table 7.

TABLE 7

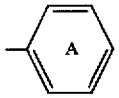

| Example No. | R¹ | R² | A | R | m.p. (°C.) | Recrystallization solvent |
|---|---|---|---|---|---|---|
| 17 | —CH$_2$S(CH$_2$)$_2$— | | 3,4-(OCH$_3$)$_2$-C$_6$H$_3$ | —N(C$_2$H$_5$)$_2$ | 115–116 | isopropyl ether-hexane |
| 18 | —CH$_2$S(CH$_2$)$_2$— | | 3,4-(OCH$_3$)$_2$-C$_6$H$_3$ | —N(CH(CH$_3$)CH$_2$CH$_3$)(CH$_2$CH$_2$CH$_3$) | 93–94 | isopropyl ether-hexane |
| 19 | —CH$_2$S(CH$_2$)$_2$— | | 3,5-(OCH$_3$)$_2$-C$_6$H$_3$ | —N(C$_2$H$_5$)$_2$ | 128–129 | isopropyl ether-hexane |
| 20 | —CH$_2$S(CH$_2$)$_2$— | | 3,4-(OCH$_3$)$_2$-C$_6$H$_3$ | 1,2,4-triazol-1-yl | 160–161 | ethyl acetate-hexane |
| 21 | —CH$_2$S(CH$_2$)$_2$— | | 3,4-(OCH$_3$)$_2$-C$_6$H$_3$ | 1,2,3-triazol-1-yl | 206–207 | ethyl acetate-hexane |
| 22 | —CH$_2$O(CH$_2$)$_2$— | | 3,4-(OCH$_3$)$_2$-C$_6$H$_3$ | —N(C$_2$H$_5$)$_2$ | 149–150 | isopropyl ether |
| 23 | CH$_3$ | CH$_3$ | 3,4,5-(OCH$_3$)$_3$-C$_6$H$_2$ | —N(C$_2$H$_5$)$_2$ | 117–118 | ethyl acetate-hexane |
| 24 | CH$_3$ | CH$_3$ | 3,4,5-(OCH$_3$)$_3$-C$_6$H$_2$ | —N(CH(CH$_3$)CH$_2$CH$_3$)(CH$_2$CH$_2$CH$_3$) | 79–80 | isopropyl ether-hexane |

TABLE 7-continued

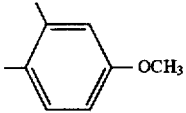

| Example No. | R¹ | R² | A | R | m.p. (°C.) | Recrystallization solvent |
|---|---|---|---|---|---|---|
| 25 | $CH_3$ | $CH_3$ | 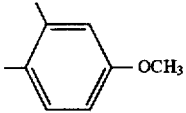 2,4-dimethoxyphenyl | $-N(C_2H_5)_2$ | 88–89 | ethyl acetate-hexane |
| 26 | $CH_3$ | $CH_3$ | 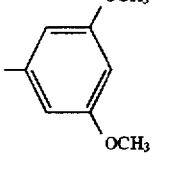 3,5-dimethoxyphenyl | $-N(C_2H_5)_2$ | 87–88 | ethyl acetate-hexane |
| 27 | $-CH_2-N(CH_3)-(CH_2)_2-$ | | 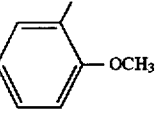 3,4-dimethoxyphenyl | $-N(C_2H_5)_2$ | 112–114 | ethyl acetate-hexane |
| 28 | $-CH_2-N(CH_2C_6H_5)-(CH_2)_2-$ | | 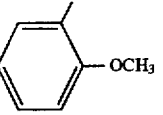 3,4-dimethoxyphenyl | $-N(C_2H_5)_2$ | 133–134 | ethyl acetate-hexane |
| 29 | $CH_3$ | $CH_3$ | 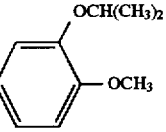 3-isopropoxy-4-methoxyphenyl | 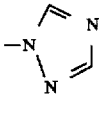 | 107–108 | ethyl acetate-hexane |
| 30 | $CH_3$ | $CH_3$ | 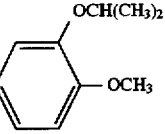 3-isopropoxy-4-methoxyphenyl | 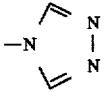 | 187–188 | ethyl acetate-hexane |
| 31 | $-CH_2-N(CH_2C_6H_5)-(CH_2)_2-$ | | 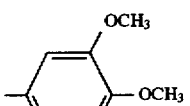 3,4-dimethoxyphenyl | 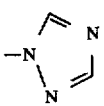 | 136–137 | ethyl acetate-hexane |
| 32 | $-CH_2-N(CH_2C_6H_5)-(CH_2)_2-$ | | 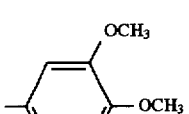 3,4-dimethoxyphenyl | 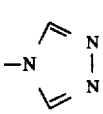 | 129–130 | ethyl acetate-hexane |

TABLE 7-continued

Structure: R¹ and R² on thiophene fused to pyridine bearing CH₂R, COOC₂H₅, and aryl group A.

| Example No. | R¹ | R² | A | R | m.p. (°C.) | Recrystallization solvent |
|---|---|---|---|---|---|---|
| 33 | —CH₂—N(CH₂C₆H₅)—(CH₂)₂— | | 2,5-(OCH₃)₂-phenyl | imidazol-1-yl | 168–169 | ethanol |
| 34 | —CH₂—N(CH₂C₆H₅)—(CH₂)₂— | | 2,5-(OCH₃)₂-phenyl | 2-(methylthio)-1-methylimidazol-... | 118–119 | ethyl acetate-hexane |
| 35 | —CH₂—N(CH₂C₆H₅)—(CH₂)₂— | | 2,3,4-(OCH₃)₃-phenyl | —N(C₂H₅)₂ | 105–106 | ethyl acetate-hexane |
| 36 | —CH₂—N(C₂H₅)—(CH₂)₂— | | 3,4-(OCH₃)₂-phenyl | —N(C₂H₅)₂ | 91–93 | ethyl acetate-hexane |
| 37 | —CH₂—N(C₃H₇)—(CH₂)₂— | | 3,4-(OCH₃)₂-phenyl | —N(C₂H₅)₂ | 97–99 | ethyl acetate-hexane |
| 38 | —CH₂—N(CH₂-4-OCH₃-C₆H₄)—(CH₂)₂— | | 3,4-(OCH₃)₂-phenyl | —N(C₂H₅)₂ | 138–139 | ethyl acetate-hexane |
| 39 | —CH₂—N(CH₂-4-OCH₃-C₆H₄)—(CH₂)₂— | | 3,4-(OCH₃)₂-phenyl | pyrrolidin-1-yl | 133–134 | ethyl acetate-hexane |
| 40 | —CH₂—N(CH₂C₆H₅)—(CH₂)₂— | | phenyl | morpholin-4-yl | 168–169 | ethyl acetate-hexane |

TABLE 7-continued

| Example No. | $R^1$ | $R^2$ | A | R | m.p. (°C.) | Recrystallization solvent |
|---|---|---|---|---|---|---|
| 41 | —CH$_2$—N(CH$_2$C$_6$H$_5$)—(CH$_2$)$_2$— | | | 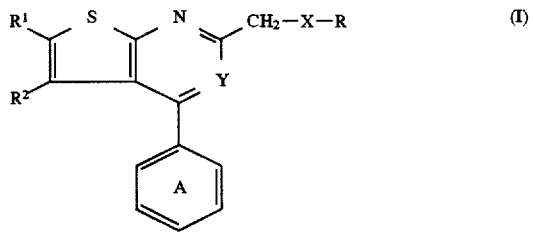 | 183–184 | ethyl acetate-hexane |

INDUSTRIAL APPLICABILITY

According to the present invention, anti-inflammatory agents, especially novel thienopyridine or thienopyrimidine derivatives useful as a therapeutic agent of arthritis, a useful agent as a bone resorption inhibitor, a method of producing them, a pharmaceutical composition containing same for the prophylaxis or treatment of an inflamatory disease or an osteoporosis are provided.

We claim:

1. A compound represented by the formula (I):

wherein $R^1$ and $R^2$ independently stand for a hydrogen atom, a halogen atom or an optionally substituted alkyl group, or $R^1$ and $R^2$ may be combined to form a 5- to 7-membered ring; Y stands for a nitrogen atom or C-G, G stands for an optionally esterified carboxyl group; X stands for an oxygen atom, an optionally oxidized sulfur atom or —(CH$_2$)$_q$— (q denotes an integer of 0 to 5); R stands for an optionally substituted heterocyclic group or an optionally substituted amino group; and ring A may optionally be substituted, or a salt thereof.

2. The compound of claim 1, wherein the optionally substituted alkyl group for $R^1$ or $R^2$ is independently a straight-chain or branched-chain C$_{1-6}$ alkyl group; the optionally substituted 5- to 7-membered ring for $R^1$ and $R^2$ is (i) a C$_{5-7}$ alicyclic hydrocarbon group, or
(ii) a heterocyclic group containing one to 4 oxygen atom, one to 4 sulfur atom which may be oxidized, or one nitrogen atom which may be substituted by optionally substituted C$_{1-10}$ alkyl;

the optionally substituted heterocyclic group for R is (i) a 5- to 7-membered heterocyclic group containing one sulfur atom, one nitrogen atom or one oxygen atom,
(ii) a 5- to 6-membered heterocyclic group containing 2 to 4 nitrogen atoms,
(iii) a 5- to 6-membered heterocyclic group containing 1 to 2 nitrogen atoms and one sulfur atom or one oxygen atom, or
(iv) a group formed by condensation of each of the above three groups (i)–(iii) with a 6-membered group containing two or less nitrogen atom, a benzene ring or a 5-membered ring containing one sulfur atom;

or the optionally substituted amino group for R is represented by -N(R$^3$) (R$^4$), in which R$^3$ and R$^4$ independently stand for a hydrogen atom, an optionally substituted hydrocarbon residue or an optionally substituted heterocyclic group, or R$^3$ and R$^4$ are combined to form a nitrogen containing cyclic group; and the ring A is substituted by a halogen atom, a nitro group, an optionally substituted alkyl group, an optionally substituted hydroxyl group, an optionally substituted thiol group, an optionally substituted amino group, an acyl group, an optionally esterified carboxyl group or an optionally substituted aromatic cyclic group.

3. The compound of claim 2, wherein the optionally substituted 5- to 7- membered ring for $R^1$ and $R^2$ is represented by the formula of —$R^1$—$R^2$—, which is —(CH$_2$)$_3$—, —(CH$_2$)$_4$—, —(CH$_2$)$_5$—, —CH$_2$—N(R$^5$)—CH$_2$—CH$_2$— (R$^5$ is C$_{1-4}$ alkyl which may be substituted by phenyl), —CH$_2$—S—CH$_2$—CH$_2$—, —CH$_2$—SO—CH$_2$—CH$_2$—, —CH$_2$—SO$_2$—CH$_2$—CH$_2$— or —CH$_2$—O—CH$_2$—CH$_2$—.

4. The compound of claim 2, wherein the optionally substituted hydrocarbon residue for R$^3$ or R$^4$ is independently a C$_{1-8}$ saturated aliphatic hydrocarbon residue,
a C$_{2-8}$ unsaturated aliphatic hydrocarbon residue,
a C$_{3-7}$ saturated alicyclic hydrocarbon residue,
a C$_{5-7}$ unsaturated alicyclic hydrocarbon residue,
a C$_{4-9}$ alicyclic-aliphatic hydrocarbon residue,
a C$_{7-9}$ phenyl alkyl, a C$_{11-13}$ naphthyl alkyl, a phenyl or a naphthyl;

the optionally substituted heterocyclic group for R$^3$ or R$^4$ is independently (i) a 5- to 7-membered heterocyclic groups containing one sulfur atom, one nitrogen atom or one oxygen atom,
(ii) a 5- or 6- membered heterocyclic groups containing 2 to 4 nitrogen atoms, or
(iii) a 5- to 6-membered heterocyclic group containing 1 to 2 nitrogen atoms and one sulfur atom or one oxygen atom, which may be condensed with a 6-membered ring containing one or two nitrogen atoms, a benzene ring or a 5-membered ring containing one sulfur atom.

5. The optionally substituted heterocyclic group for $R^3$ or $R^4$ is independently an aromatic monocyclic-heterocyclic group, an aromatic condensed heterocyclic group, or a non-aromatic heterocyclic group.

6. The compound of claim 5, wherein (i) the aromatic monocyclic-heterocyclic group for $R^3$ or $R^4$ is independently furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl or triazinyl;

(ii) the aromatic condensed heterocyclic group for $R^3$ or $R^4$ is independently benzofuranyl, isobenzofuranyl, benzo[b]thienyl, indolyl, isoindolyl, 1H-indazolyl, benzimidazolyl, benzoxazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,2-b]pyridazinyl, imidazo[1,2-b]pyrimidinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl or 1,2,4-triazolo[4,3-b]pyridazinyl; or (iii) the non-aromatic heterocyclic group for $R^3$ or $R^4$ is independently oxiranyl, azetidinyl, oxetanyl, thietanyl, pyrrolidinyl, tetrahydrofuryl, thiolanyl, piperidyl, tetrahydropyranyl, morpholinyl, thiomorpholinyl or piperazinyl.

7. The compound of claim 2, wherein R is independently 1-pyrrolidinyl, 1-imidazolidinyl, 1-pyrazolidinyl, 1-piperidinyl, piperadino, 1-piperazinyl, 4-morpholinyl, morpholino, 4-thiomorpholinyl, homopiperazin-1-yl, pyrazol-1-yl, 1,2,3-triazol-1-yl, 1,2,3-triazol-2-yl, tetrazol-1-yl, benzimidazol-1-yl, indol-1-yl or indazol-1-yl.

8. The compound of claim 2, wherein the optionally substituted hydrocarbon residue for $R^3$ or $R^4$ is independently a straight- or a branched-chain $C_{1-6}$ alkyl.

9. The compound of claim 2, wherein as a substituent for ring A, (i) the halogen atom is fluorine, chlorine, bromine or iodine;

(ii) the optionally substituted alkyl group is $C_{1-10}$ straight-chain alkyl, $C_{3-10}$ branched-chain alkyl or $C_{3-10}$ cyclic alkyl;

(iii) the optionally substituted hydroxyl group is hydroxyl, $C_{1-10}$ alkoxy, $C_{2-10}$ alkenyloxy, $C_{2-10}$ alkynyloxy, phenyl-$C_{1-4}$ alkyloxy, $C_{2-4}$ alkanoyloxy, phenoxy or 4-chlorophenoxy;

(iv) the optionally substituted thiol group is thiol group, $C_{1-10}$ alkylthio, $C_{2-10}$ alkenylthio, $C_{2-10}$ alkynylthio, phenyl-$C_{1-4}$ alkylthio, $C_{2-4}$ alkanoylthio or phenylthio;

(v) the optionally substituted amino group is amino group which may be substituted by $C_{1-10}$ alkyl, $C_{2-10}$ alkenyl, $C_{2-10}$ alkynyl, aromatic group, heterocyclic group or $C_{1-10}$ acyl group;

(vi) the acyl group is formyl or ones formed by bonding of $C_{1-10}$ alkyl, $C_{2-10}$ alkenyl, $C_{2-10}$ alkynyl or an aromatic group with carbonyl group;

(vii) the optionally esterified carboxyl group is a group represented by the formula —COOR$^6$, wherein R$^6$ is a hydrogen atom, $C_{1-6}$ alkyl group, aryl-$C_{1-6}$ alkyl group or aryl group;

(viii) the optionally substituted aromatic cyclic group is $C_{6-14}$ aromatic hydrocarbon group or aromatic heterocyclic group.

10. The compound of claim 1, wherein G is a group represented by the formula —COOR$^6$ is a hydrogen atom, a $C_{1-6}$ alkyl, an aryl-$C_{1-6}$ alkyl or an aryl.

11. The compound of claim 1, wherein X is —$(CH_2)_q$— (q is an integer of 0 to 3).

12. The compound of claim 11, wherein q is 0.

13. The compound of claim 1, wherein the ring A is substituted by at least one $C_{1-6}$ alkoxy.

14. The compound of claim 1, which is

Ethyl 6-(N,N-diethylaminomethyl)-4-(3,4-dimethoxyphenyl)-2,3-dimethylthieno[2,3-b]pyridine-5-carboxylate.

4-(3,4-Dimethoxyphenyl)-2-(N,N-diethylaminomethyl)-5,6 -dimethylthieno[2,3-d]pyrimidine.

Ethyl 2-(N,N-diethylaminomethyl)-4-(3,4-dimethoxyphenyl)-5,6-dihydro-8H-thiopyrano[4',3':4,5]thieno[2,3-b]pyridine-3-carboxylate.

Ethyl 4-(3,4-dimethoxyphenyl)-5,6-dihydro-2-(1,2,4-triazol-1-ylmethyl)-8H-thiopyrano[4',3':4,5]thieno[2,3-b]pyridine-3-carboxylate.

Ethyl 2-(N,N-diethylaminomethyl)-4-(3,4-dimethoxyphenyl)-5,6-dihydro-8H-pyrano[4',3':4,5]thieno[2,3-b]pyridine-3-carboxylate.

Ethyl 2-(N,N-diethylaminomethyl)-4-(3,4-dimethoxyphenyl)-7-methyl-5,6,7,8-tetrahydrothieno[2,3-b:5,4-c']dipyridine-3-carboxylate.

Ethyl 7-benzyl-2-(N,N-diethylaminomethyl)-4-(3,4-dimethoxyphenyl)-5,6,7,8-tetrahydrothieno[2,3-b:5,4-c']dipyridine-3-carboxylate.

Ethyl 7-benzyl-4-(3,4-dimethoxyphenyl)-5,6,7,8-tetrahydro-2-(1,2,4-triazol-1-ylmethyl)thieno[2,3-b:5,4-c']dipyridine-3-carboxylate.

Ethyl 7-benzyl-4-(3,5-dimethoxyphenyl)-5,6,7,8-tetrahydro-2-(1-methylimidazol-2-ylthiomethyl)thieno[2,3-b:5,4-c']dipyridine-3-carboxylate.

Ethyl 2-(N,N-diethylaminomethyl)-4-(3,4-dimethoxyphenyl)-7-propyl-5,6,7,8-tetrahydrothieno[2,3-b:5,4-c']dipyridine-3-carboxylate.

Ethyl 7-(4-methoxybenzyl)-4-(3,4-dimethoxyphenyl)-2-pyrrolidinomethyl-5,6,7,8-tetrahydrothieno[2,3-b:5,4-c']dipyridine-3-carboxylate.

15. A method of producing a compound represented by the formula (I-1)

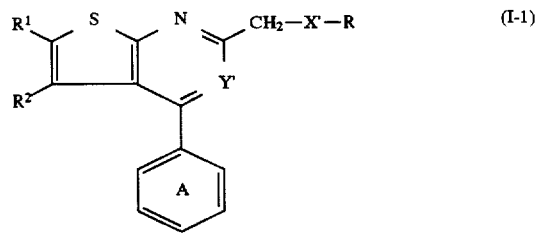

wherein $R^1$, $R^2$, R and ring A are of the same meaning as defined in claim 1, X' is an oxygen atom or a sulfur atom and Y' is a nitrogen atom or C-G' (G' is an esterified carboxyl group); which is characterized by allowing a compound represented by the formula (II-1)

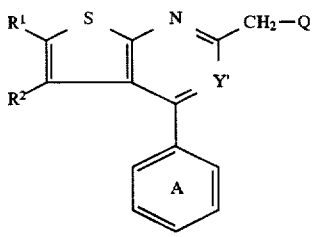
(II-1)

wherein Q is a leaving group; and other symbols are of the same meaning as defined above, to react with a compound represented by the formula (III)

R-X'H  (III)

wherein X' and R are of the same meaning as defined above.

16. A method of producing a compound represented by the formula (I-2)

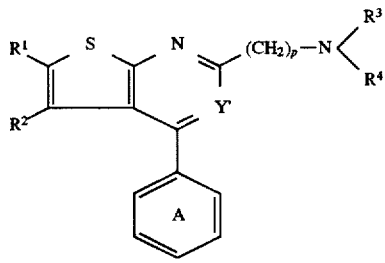
(I-2)

wherein $R^1$, $R^2$ and ring A are of the same meaning as defined in claim 1; $R^3$ and $R^4$ independently stand for a hydrogen atom, an optionally substituted hydrocarbon residue or an optionally substituted heterocyclic group, or $R^3$ and $R^4$ may be combined to form a nitrogen containing ring; Y' stands for a nitrogen atom or C-G' (G' is an esterified carboxyl group); and p is an integer of 1 to 6, which is characterized by allowing a compound represented by the formula (II-2)

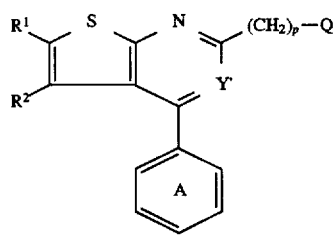
(II-2)

wherein Q is a leaving group; and other symbols are of the same meaning as defined above, to react with a compound represented by the formula (IV)

HNR³R⁴  (IV)

wherein $R^3$ and $R^4$ are of the same meaning as defined above.

17. A method of producing a compound represented by the formula (I-4)

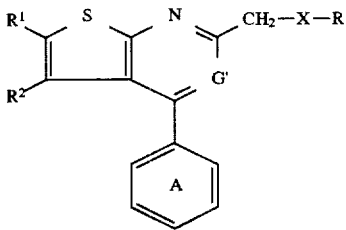
(I-4)

wherein $R^1$, $R^2$, X, R and ring A are of the same meaning as defined in claim 1; and G' is an esterified carboxyl group; which is characterized by allowing a compound represented by the formula (VIII)

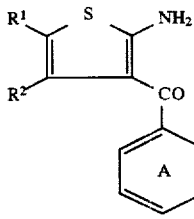
(VIII)

wherein $R^1$, $R^2$ and ring A are of the same meaning as defined above, to react with a compound represented by the formula (IX)

R-X—CH₂COCH₂—G'  (IX)

wherein R, X and G' are of the same meaning as defined above.

18. A composition which comprises a compound represented by the formula (I):

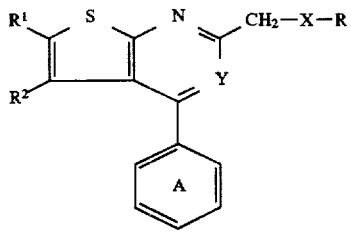
(I)

wherein $R^1$ and $R^2$ independently stand for a hydrogen atom, a halogen atom or an optionally substituted alkyl group, or $R^1$ and $R^2$ may be combined to form an optionally substituted 5- to 7-membered ring; Y is a nitrogen atom or C-G, G is an optionally esterified carboxyl group; X is an oxygen atom, an optionally oxidized sulfur atom or —(CH₂)$_q$— (q is an integer of 0 to 5); R is an optionally substituted heterocyclic group or an optionally substituted amino group; and ring A may optionally be substituted; or a salt thereof.

19. The pharmaceutical composition which comprises a compound of claim 18.

20. The pharmaceutical composition of claim 19, which is for the prophylaxis or treatment of an inflammatony disease.

21. The pharmaceutical composition of claim 19, which is for promoting anti-pyretic analgesic action.

22. The pharmaceutical composition of claim 19, which is for the prophylaxis or treatment of arthritis.

23. The pharmaceutical composition of claim 19, which is for inhibiting bone resorption.

24. The pharmaceutical composition of claim 19, which is for the prophylaxis or treatment of osteoporosis.

25. The pharmaceutical composition of claim 19, which is for supressing the production of cytokine in a mammal.

26. A method for the prophylaxis or treatment of an inflammatony disease in a mammal which comprises administering a pharmaceutically effective amount of a compound of claim 18 to said mammal in need thereof.

27. A method for the prophylaxis or treatment of osteoporosis in a mammal which comprises administering a pharmaceutically effective amount of a compound of claim 18 to said mammal in need thereof.

\* \* \* \* \*